(12) United States Patent  
McClung, III

(10) Patent No.: US 9,023,275 B2  
(45) Date of Patent: May 5, 2015

(54) SHALE SHAKERS AND SEPARATORS WITH REAL TIME MONITORING OF OPERATION AND SCREENS, KILLING OF LIVING THINGS IN FLUIDS, AND HEATER APPARATUS FOR HEATING FLUIDS

(76) Inventor: Guy L. McClung, III, Rockport, TX (US)

(*) Notice: Subject to any disclaimer, the term of this patent is extended or adjusted under 35 U.S.C. 154(b) by 642 days.

(21) Appl. No.: 13/374,243

(22) Filed: Dec. 16, 2011

(65) Prior Publication Data

US 2012/0222854 A1  Sep. 6, 2012

Related U.S. Application Data

(63) Continuation-in-part of application No. 13/373,283, filed on Nov. 9, 2011.

(60) Provisional application No. 61/458,444, filed on Nov. 22, 2010, provisional application No. 61/519,054, filed on May 16, 2011, provisional application No. 61/465,783, filed on Mar. 24, 2011, provisional application No. 61/465,132, filed on Mar. 15, 2011.

(51) Int. Cl.
| | | |
|---|---|---|
| A61L 2/00 | (2006.01) |
| A61L 2/18 | (2006.01) |
| A61L 9/00 | (2006.01) |
| E21B 21/06 | (2006.01) |
| E21B 43/08 | (2006.01) |
| C02F 1/36 | (2006.01) |
| H01L 41/113 | (2006.01) |
| H02N 2/18 | (2006.01) |
| A61L 2/03 | (2006.01) |

(52) U.S. Cl.
CPC ............... *E21B 21/065* (2013.01); *C02F 1/36* (2013.01); *E21B 43/088* (2013.01); *H01L 41/113* (2013.01); *H02N 2/186* (2013.01); *A61L 2/03* (2013.01)

(58) Field of Classification Search
USPC .................................................. 422/22, 28, 32
See application file for complete search history.

(56) References Cited

U.S. PATENT DOCUMENTS

| | | | | |
|---|---|---|---|---|
| 3,289,775 | A | * | 12/1966 | Stone ............................... 175/66 |
| 3,963,605 | A | | 6/1976 | Seabourn .......................... 209/2 |
| 4,340,469 | A | | 7/1982 | Archer ........................... 209/315 |
| 5,190,645 | A | | 3/1993 | Burgess ......................... 210/144 |
| 5,221,008 | A | | 6/1993 | Derrick, Jr. et al. .......... 209/269 |
| 5,305,886 | A | * | 4/1994 | Kehl et al. .......................... 209/2 |
| 6,032,806 | A | | 3/2000 | Leone et al. ................... 209/402 |
| 6,333,700 | B1 | | 12/2001 | Thomeer et al. ............ 340/854.8 |
| 6,543,620 | B2 | | 4/2003 | Allaei ......................... 209/365.1 |
| 6,564,947 | B2 | | 5/2003 | Bakula .......................... 210/388 |
| 6,868,972 | B2 | | 3/2005 | Seyffert et al. ............... 209/254 |
| 7,198,156 | B2 | | 4/2007 | Schulte et al. ................ 209/309 |

(Continued)

OTHER PUBLICATIONS

U.S. Appl. No. 61/314,736, Olivier et al., filed Mar. 17, 2010.*

*Primary Examiner* — Regina M Yoo  
(74) *Attorney, Agent, or Firm* — Guy McClung

(57) ABSTRACT

Separators and shakers are disclosed with real time monitoring of screen condition; killing apparatus for killing living things in fluid flowing from a separator or shaker; and/or heating apparatus for heating material fed to or flowing from a separator or shaker. This abstract is provided to comply with the rules requiring an abstract which will allow a searcher or other reader to quickly ascertain the subject matter of the technical disclosure and is submitted with the understanding that it will not be used to interpret or limit the scope or meaning of the claims, 37 C.F.R. 1.72(b).

8 Claims, 12 Drawing Sheets

(56) References Cited

U.S. PATENT DOCUMENTS

| | | | |
|---|---|---|---|
| 7,264,125 B2 | 9/2007 | Lipa | 209/397 |
| 7,303,079 B2 | 12/2007 | Reid-Robertson et al. | 209/405 |
| 7,331,469 B2 | 2/2008 | Padalino et al. | 209/413 |
| 7,484,625 B2 | 2/2009 | Scott et al. | 209/404 |
| 7,571,817 B2 | 8/2009 | Scott et al. | 209/413 |
| 7,581,647 B2 | 9/2009 | Grichar et al. | 209/370 |
| 7,909,170 B2 | 3/2011 | Jones et al. | 209/380 |
| 7,992,719 B2 | 8/2011 | Carr et al. | 209/405 |
| 8,141,714 B2 | 3/2012 | Burkhard | 209/365.1 |
| 8,141,715 B2 | 3/2012 | Helmy | 209/403 |
| 8,151,994 B2 | 4/2012 | Carr et al. | 209/325 |
| 2006/0113220 A1 | 6/2006 | Scott et al. | 209/250 |
| 2009/0283454 A1 | 11/2009 | Scott et al. | 209/552 |
| 2012/0110901 A1* | 5/2012 | Olivier et al. | 44/605 |

\* cited by examiner

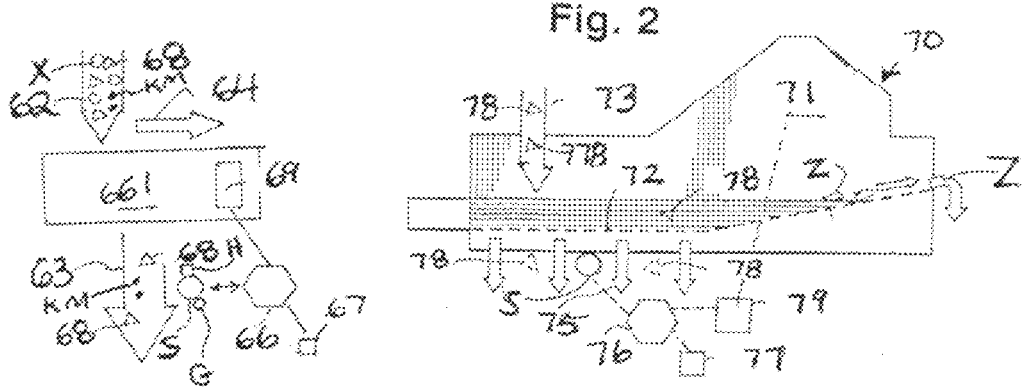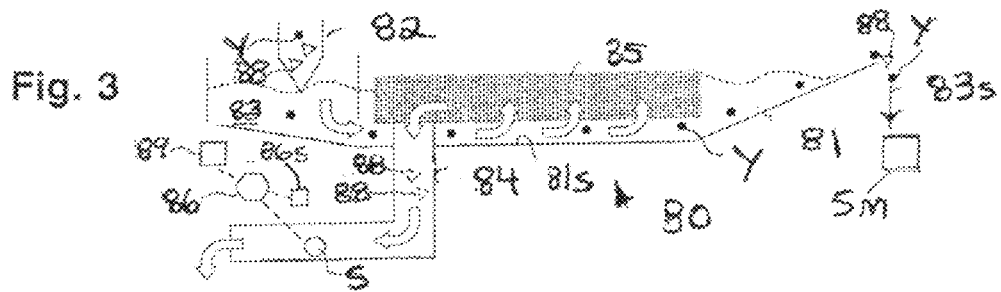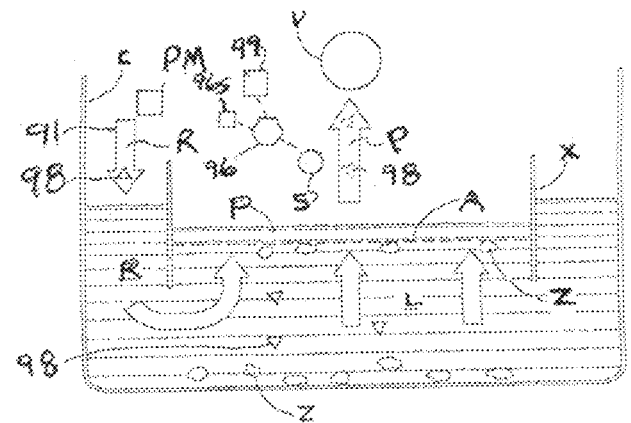

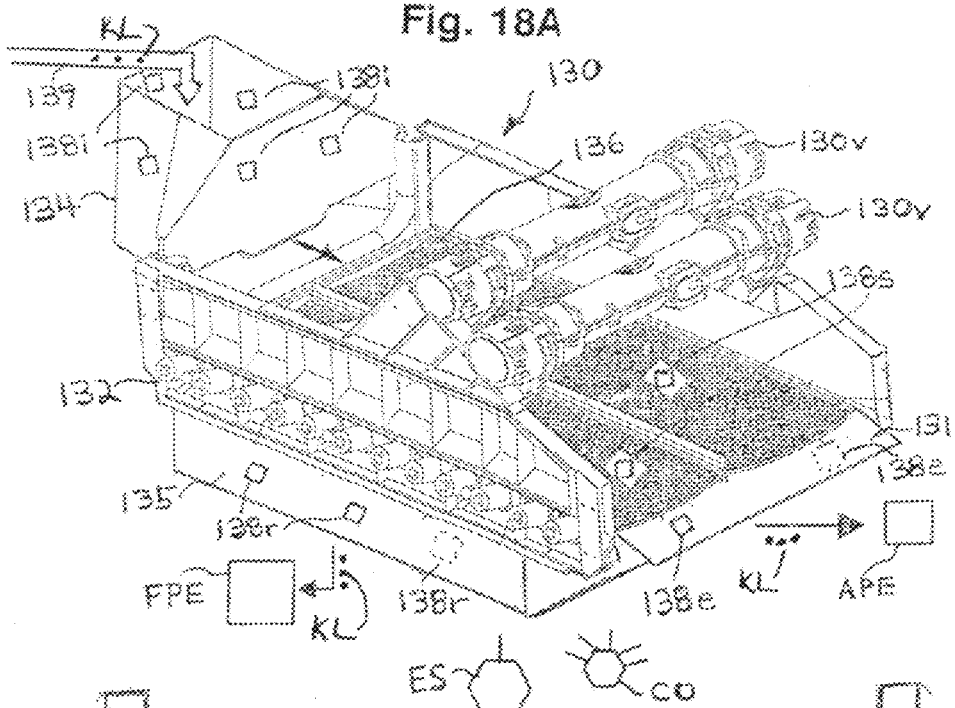
Fig. 18A
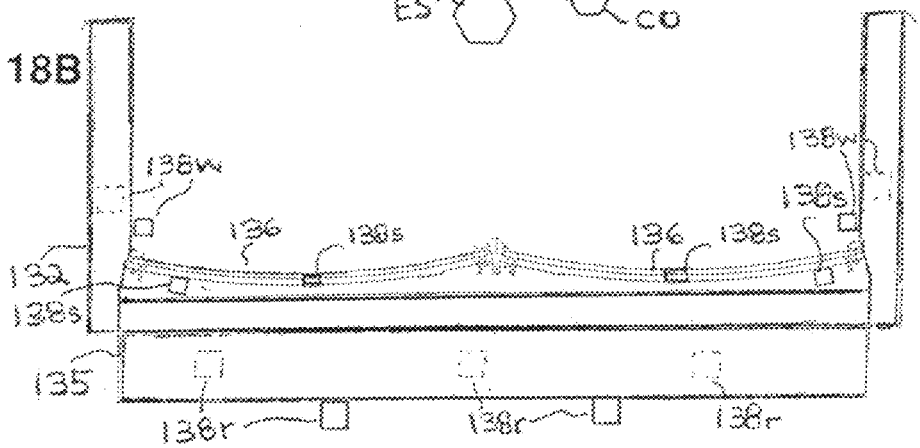
Fig. 18B
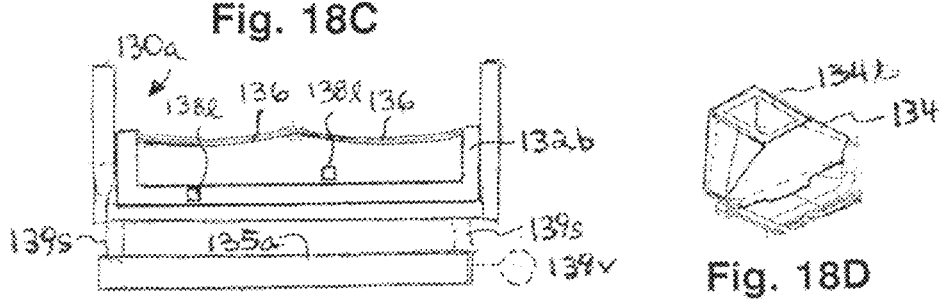
Fig. 18C
Fig. 18D

Fig. 23
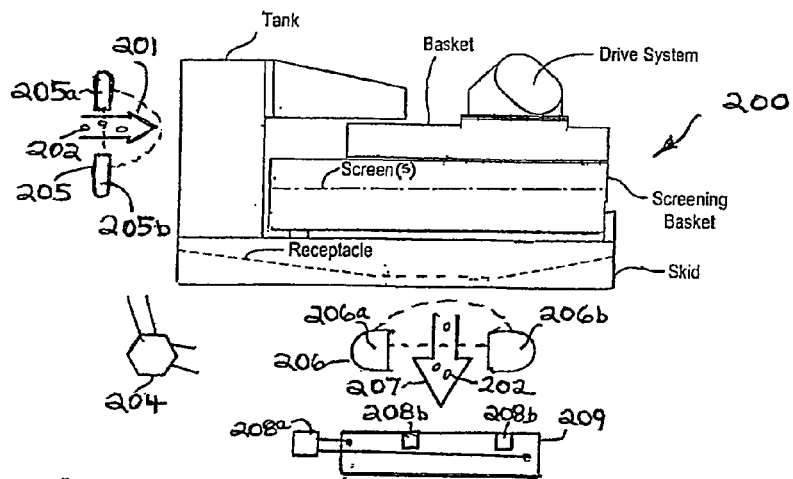
Fig. 24A
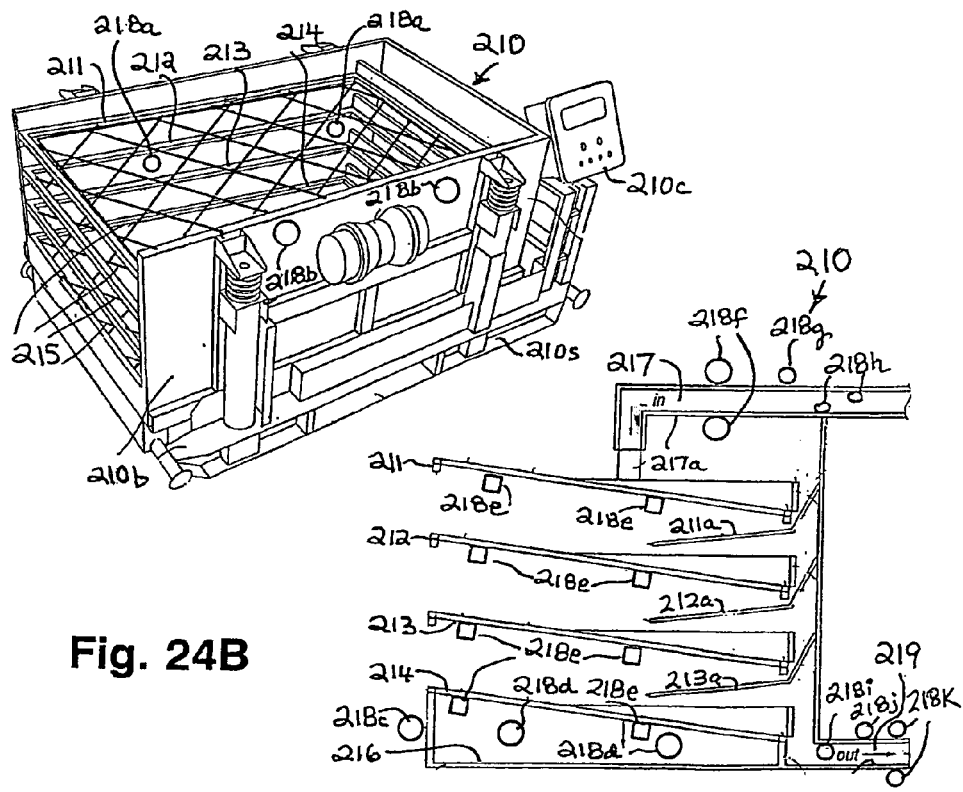
Fig. 24B

SHALE SHAKERS AND SEPARATORS WITH REAL TIME MONITORING OF OPERATION AND SCREENS, KILLING OF LIVING THINGS IN FLUIDS, AND HEATER APPARATUS FOR HEATING FLUIDS

CROSS REFERENCE TO RELATED APPLICATIONS

This is a continuation-in-part of U.S. application Ser. No. 13/373,283 filed Nov. 9, 2011 which claims priority from U.S. Application Ser. No. 61/458,444 filed Nov. 22, 2011. The present invention and application claim priority under the Patent Laws from pending U.S. Application Ser. Nos.: 61/519,054 filed May 16, 2011; 61/458,444 filed Nov. 22, 2010; 13/373,283 filed Nov. 9, 2011; 61/465,783 filed Mar. 24, 2011; and 61/465,132 filed Mar. 15, 2011.

BACKGROUND OF THE INVENTION

1. Field of the Invention

The present invention is directed to: vibratory separators, systems using such separators, and methods of their use; in certain aspects to shale shakers; in certain particular aspects, to such systems with detection capability for detecting material flowing from such a separator or shaker, optionally with treatment of material; monitoring vibratory separator operation; monitoring and/or inspecting screening apparatus on a vibratory separator; discovering faults and/or tears in a screen apparatus; and, in certain particular aspects, to real-time monitoring of shake shaker operation and efficiency and/or to-real-time inspection of shaker screens for wear, misplacement, and/or tearing of screening material.

2. Description of Related Art

There are a wide variety of known vibratory separators, shakers, and methods of their use, some of which are disclosed in numerous issued U.S. patents and published patent applications.

A variety of nano RFID devices are known, see, e.g., U.S. patent application Ser. Nos. 12/501,909 filed Jul. 13, 2009; 12/498,689 filed Jul. 7, 2009; and 12/497,193 filed Jul. 2, 2009—all of which are incorporated fully herein for all purposes.

A variety of micro-resonant devices are known, see, e.g., U.S. patent application Ser. No. 11/913,661 published Jan. 29, 2009, Pub. No. 2009/0027280 A1, incorporated fully herein for all purposes.

A variety of nanodevices including nanorobots are known, see, e.g., U.S. patent application Ser. Nos. 12/604,310 filed Oct. 22, 2009 which is incorporated fully herein for all purposes. As defined below, for purposes of this invention and this application, McNano devices includes, inter alia, the devices disclosed referred to in, and disclosed in references cited in the five patent applications referred to above in this paragraph and in the two preceding paragraphs.

BRIEF SUMMARY OF THE INVENTION

The present invention, in certain aspects, discloses vibratory separators with: real time monitoring of operation and/or of screen(s); killing ability to kill living things in fluids flowing to and/or from a separator or shaker; and/or heating ability to heat such fluids. In certain aspects such a separator ro shaker has detection apparatus for detecting material exiting from a vibratory separator. In certain particular aspects, the vibratory separator is a shale shaker used in wellbore operations. In certain aspects, detectable material is applied to one, two, or both streams from a separator or shaker; e.g., a cleaned stream and a stream with material that is separated from the cleaned stream.

The present invention, in certain aspects, discloses such a separator in which one or a plurality of detectors detect detectable material in one or in a plurality of streams flowing from a separator. In one aspect in which the separator is a shale shaker, one or a plurality of detectors detect material in a stream from a top of screen apparatus, from a stream that has flowed through screen apparatus, or both.

In certain aspects, detectable material is introduced either into an initial stream fed to a separator or into a receiver that receives an initial stream. In another aspect, detectable material is fed separately to a component or components of a separator system. In one aspect in which the separator is a shale shaker, detectable material is applied to, introduced into, or fed to one, two, or all three of: initial feed stream itself; receptacle, tank, or "possum belly" into which an initial stream is introduced; and/or directly onto screening apparatus of the shale shaker (with a screen or screens essentially all at one general level or with a screen or screens at two, three, four or more distinct levels). Optionally, killing material is added into any of these structures or streams to kill living things therein.

In certain aspects, detectable material of one kind is used. In other aspects, multiple detectable materials are used, either: all in one stream (multiple different materials fed into a single stream or multiple different materials fed into different streams); or different detectable materials are fed into different streams at different locations in an overall system. In one aspect, a first detectable material is fed into a bottom exit stream containing drilling fluid that has flowed through screening apparatus of a shale shaker and a second different detectable material is fed into a second stream containing cuttings, etc. which flows from the top of the screening apparatus. Such materials can act as an identifier for a stream into which they are introduced. Optionally, a third detectable material, different from the first and second, is fed into the initial feed stream to the shaker. In FIG. 1, the material DM may be any of these.

In certain embodiments, in separators with multiple separating elements, different detectable material is fed to different elements so that a stream or streams exiting an element is testable to ascertain if the element is accomplishing the desired task, e.g., but not limited to, performing a desired separation of stream components. In one particular aspect, in a shale shaker with multiple screens (whether at generally the same level or at different levels), different detectable material can be flowed to each screen so that flow from each particular screen is identifiable, either flow from the top of a screen or flow through and out from a screen (from the top or from the bottom depending on whether the shaker is a down-flow shaker or an up-flow shaker). The present invention includes within its scope: down-flow systems in which the general flow regime is initial flow of a primary stream to screen top(s), with a secondary stream flowing from the top of the screen(s) and a tertiary stream flowing through the screen(s) and out the screen bottoms; and up-flow systems in which an initial stream is pumped below screen(s) and fluid to be recovered flows out through the top of screen(s).

The present invention, in certain aspects, discloses a separator in which one or a plurality of detectors detect detectable material in one or in a plurality of streams flowing from a separator. In one aspect in which the separator is a shale shaker, one or a plurality of detectors detect material in a first stream flowing off from a top of screen apparatus, from a second stream flowing down and out from screen apparatus, or both; or, in an upflow shaker, in a first stream flowing through a screen, in a second stream that does not flow through a screen, or both.

In certain embodiments, a control system is in communication (on-site, remote, or both) with a detector or detectors used for detecting detectable material in one stream or in multiple streams of a separation system. In one aspect in which the separator is a shale shaker, a first detector detects detectable material in a first separated stream that contains cuttings, debris, etc. and a second detector detects detectable material in a second stream containing drilling fluid without the cuttings, debris, etc. that have been separated out in the first separated stream (the shaker being either an upflow shaker or a downflow shaker); and the control system in communication with both the first detector and with the second detector.

In certain aspects, in a system according to the present invention having a control system, the control system can be in communication with every operable mechanism, detector, and system associated with the separation and can provide a variety of functions and operations in response to the detection of detected material in a stream produced by a separator or shaker; including, but not limited to continuation of stream monitoring, e.g. until a level of detected material changes or until a certain type of detectable material is detected;

system shut down, e.g., shut down of a pumping system that supplies fluid or actuation of conduit apparatus or valve apparatus to divert flow from a separator or from part of a system;

provision of an alarm, on-site, remote, or both, e.g., a sound alarm, visual alarm, chart alarm, and/or signal alarm;

diversion of fluid to be treated to a different separator, tank, or other apparatus;

selection or de-selection of a specific separation element and/or screen;

introduction of detectable material into a primary stream to provide identification of the primary stream or of a secondary stream whose source is the primary stream;

provision of heat to a stream;

provision of killing material or sterilizing material to a stream to kill living things therein;

provision of electric current to a stream;

provision of microwaves to a stream;

provision of more of a detectable material to a stream and/or provision of a different detectable material to a stream; and/or provision of killing or sterilizing heat, current, signals, microwaves, or material to a stream when specified living things are present or are detected.

In such embodiments, appropriate treatment systems, conduits, valves, pumps, material applicators, regulators, gauges, devices, and/or apparatuses are used in conjunction with the control system at appropriate locations in the system to effect the desired function or result.

In certain aspects, the detectable material is one of or a combination of: light reflective material; specific detectable chemical material; fluorescent material; colored material; electrically conductive material; material whose presence changes an electric filed or magnetic field; detectable living things; material (e.g., things, particles, items, objects, and/or solids) of known size or known largest dimension; material whose presence changes or responds to microwaves applied to a stream; very small devices or apparatuses, e.g., McNanos or McNano devices; and material that changes or responds to sound waves applied to a stream. An appropriate detector is used for each of these detectable materials. When multiple such materials are used, a detector or detectors are used to detect each type of detectable material.

Detectable material can be used to provide an indication of separation effectiveness. Detectable material can provide an indication of correct or incorrect screen mounting in a shale shaker. Detectable material can provide an indication of insufficient screen sealing in a shale shaker. Detectable material of a known size can provide an indication of screen effectiveness and/or of screen condition. All of these can be done in real time.

In one example, a stream of drilling fluid with drilled cuttings is pumped to the screens of a shale shaker with detectable material with particles of known size added to the stream, a known size which is larger than the size of particles that can pass through the screens (when the screens are properly mounted and sealed and in good condition). If none of the detectable material is detected in the fluid flowing down from the screens (fluid which has passed through the screens), this is an indication that the screens are not worn, damaged, or torn and that they are mounted properly. If detectable material is detected in the fluid flowing through and down from the screens, this is an indication that either the screens are damaged, worn or torn, or they are not mounted or sealed properly, or both.

In one example, a stream of drilling fluid with drilled cuttings is pumped to the screens of a shale shaker with detectable material with particles of known size added to the stream, a known size which is the same as or smaller than openings in the screens so that the detectable material is passable throught the screens. If the detectable material is detected in the fluid flowing down from the screens (fluid which has passed through the screens), this is an indication that the screens are performing as desired. If detectable material is not detected in the fluid flowing down from the screens, this can be an indication that either the screens are clogged or damaged, or that the information given for the screens was in error. If detectable material is detected in the fluid flowing off the top of the screens, this can be an indication that either the screens are clogged, damaged, or that the information given for the screens was in error.

In one aspect, detectable material as described in each of the two preceding paragraphs is fed simultaneously to screen (s) of a shaker and detection of the materials in either a top stream or a bottom stream or both provides the information related to each material.

The present invention provides, in certain aspects, methods for checking the operation of a vibratory separator that include feeding to the vibratory separator detectable material, e.g., but not limited to, things, particles, items, objects, and/or solids of known size ("things") and then sensing such material either by monitoring an electric current of a stream with such things in the stream or by monitoring a stream with such things in the stream, the things having, e.g., a characteristic or property of being lit up by a beam or beams of ultraviolet light and/or the things being very small, e.g., McNanos or McNano devices. In one aspect, a stream with things of a known size is fed to the separator or shaker with a screen or screens that are chosen to screen out things of the known size.

Monitoring (e.g., via either sensing of level of electrical current in the output stream and/or the presence of things that react to ultraviolet light and/or monitoring of very small devices) an output stream from the screen(s) indicates the presence of the things in the output stream, indicating that the screen(s) did not screen out the things—and that, therefore, the screen is damaged, torn, worn, and/or installed incorrectly and/or not sealed in place.

The present invention provides, in certain aspects, methods for checking the operation of a vibratory separator that include feeding to the vibratory separator things, particles, items, objects, and/or solids of known size ("things") and then sensing such things either by monitoring an electric current of a stream with such things in the stream or by monitoring a stream with such things in the stream, the things having the characteristic of being lit up by a beam or beams of ultraviolet light.

The present invention discloses, in certain aspects, fluorescence monitoring of a screen or screens used in a vibratory separator or shale shaker. In certain methods, fluorescence of material flowing to a screen is monitored to detect if any of the material has passed through the screen. Material that fluoresces in response to UV light is accurately sized and material of a known size, that a screen is supposed to screen out, is introduced into the fluid being fed to the shaker. If the screen is operating properly and is not damaged, none of this sized fluorescent material passes through the screen. If the screen is torn or damaged so that it no longer screens out material of the size of the sized fluorescent material, this material passes through the screen. Fluid with material passing through the screen is subjected to a beam of ultraviolet light. If the material fluoresces, this indicates that the screen is damaged. This fluorescence can be detected visually and/or with an optical detection system. The system can be set to provide a warning; provide an alarm; and/or to shut the shaker down. The sized fluorescent material can be fed continuously to the shaker in the fluid feed or it can be fed intermittently if only periodic inspection is desired.

The present invention discloses, in certain aspects, electrical conductivity monitoring of a screen or screens used in a vibratory separator or shale shaker. In certain methods the electrical conductivity of screened fluid exiting from the bottom of a shaker screen is monitored and material particles of known size are introduced into the feed of fluid to the shaker. An inspection system determines base levels for the electrical conductivity of the fluid when the particles are not present. If and when the system detects a change in measured electrical conductivity of the fluid stream, this indicates that the sized particles, which should have been screened out on the top of the screening material, have however passed through the screening material, indicating a tear in the screening material or damage to it that allows the sized particles to pass through the screen. The system can be set to provide a warning; provide an alarm; and/or to shut the shaker down. The sized particles can be fed continuously to the shaker in the fluid feed or they can be fed intermittently if only periodic inspection is desired.

The present invention discloses, in certain aspects, vibration monitoring of a piezoelectric sensor or sensors on a separator, on a shaker, and/or on a screen or screens used in a vibratory separator or shale shaker. Piezoelectric materials output an electric current in response to vibration. If the vibration changes, the level of the output current changes. A screen and/or its mounting will vibrate differently if the screening material on the screen is torn or damaged as compared to its vibration when the screen is undamaged and not torn. A piezoelectric sensor on a separator, shaker, or screen senses a change in vibration due to screen damage or due to screen misalingment or poor sealing, and this change is reflected in a change in the current output by the piezoelectric sensor [as compared to its output when the screen is undamaged and is operating properly].

The present invention discloses, in certain aspects, monitoring of a NanoTag, McNanos, or Nanotransmitter sensor or sensors on or used with a vibratory separator or shale shaker. NanoTags, Mcnanos, and/or Nanotransmitters of a specific known size are fed to a separator, shaker, or screen which should, if used properly and if screening material is undamaged, prevent the passage through the screen's screening material of the McNanos, NanoTags and/or NanoTransmitters. A screen's output fluid is monitored for the presence of the NanoTags and/or NanoTransmitters. Detection of either of these Nano Devices indicates a problem—e.g., either improper screen mounting or sealing, torn or damaged screening material, or both.

Accordingly, the present invention includes features and advantages which are believed to enable it to advance elastomer technology. Characteristics and advantages of the present invention described above and additional features and benefits will be readily apparent to those skilled in the art upon consideration of the following detailed description of preferred embodiments and referring to the accompanying drawings.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures.

It is, therefore, an object of at least certain preferred embodiments of the present invention to provide:

New, useful unique, efficient, nonobvious separators and shakers and methods of their use.

New, useful, unique, efficient, nonobvious devices, systems and methods for monitoring operation and efficiency of a vibratory separator or shale shaker, in one aspect, in real time.

New, useful unique, efficient, nonobvious methods of use of separators and shakers with apparatus, devices, and/or systems for monitoring status and condition of a screen for a vibratory separator or for a shale shaker, in one aspect, in real time.

New, useful, unique, efficient, nonobvious vibratory separators and shale shakers that provide: real time monitoring of operation, real time monitoring of status and condition of a screen or screens, killing apparatus for killing living things in fluids flowing to and/or from a separator or shaker, and/or apparatus and/or structure for heating fluids flowing to and/or from a separator or shaker.

The present invention, in certain aspects, discloses a screen for a vibratory separator, the screen including: a body, screening material on the body through which material is passable, piezoelectric apparatus in or on the body for producing electric current in response to vibration of the body, electrically conductive material in or on the body and connected to the piezoelectric generator, the piezoelectric apparatus for supplying electric current to the electrically conductive material. In one aspect, the electrically conductive material is resistively heated when the screen vibrates. "Electrically conductive material" and "conductor" as used herein include any system, circuit, cables, wires, electrodes, connections, and/or conductor arrangement that is/are usable to conduct current in a circuit and, in certain aspects, to effect the killing of living things or to produce the desired reisistive heating of an element, wire, or part; or to produce the desired electric current in a completed circuit that flows to material being processed.

In one aspect, the vibratory separator is a shale shaker for processing drilling fluid with solids therein and the screening material is for screening out solids from the drilling fluid with solids therein.

In certain aspects, the present invention discloses a vibratory separator that includes: a screen support, vibratory apparatus for vibrating the screen support, screen apparatus supported by the screen support, the screen apparatus vibratable when the screen support is vibrated, the screen apparatus for screening material introduced to the vibratory separator, the screen apparatus including a body and screening material connected to the body through which material is passable, piezoelectric apparatus in or on the body for producing electric current in response to vibration of the body, electrically conductive material in or on the body and connected to the piezoelectric apparatus, the piezoelectric apparatus for supplying electric current to the electrically conductive material. In one aspect, the vibratory separator is a shale shaker for processing drilling fluid with solids therein and the screening material is for screening out solids from the drilling fluid with solids therein. Optionally, a material introduction structure and/or the screen support, e.g., but not limited a basket, may have one or more piezoelectric combinations or generators on its walls, end(s), and/or bottom. These piezoelectric devices, in certain aspects, provide material heating, and/or current for killing living things.

With any such vibratory apparatus there may be a control system or control apparatus for controlling the vibratory apparatus and the piezoelectric device(s). In one aspect, the control apparatus receives signals from the piezoelectric device(s) corresponding to vibration (e.g., of the screen apparatus, of the basket, and/or of the material introduction structure) and in response to said signals can change vibrations produced by the vibratory apparatus, e.g. to change vibration of the screen apparatus. In one aspect, the signals are indicative of status of the screening material. In one aspect, the signals indicate damage to the screening material and the control apparatus can change the vibration level or can turn off the vibratory apparatus after receipt of the signals.

The present invention discloses, in certain aspects an applicator for applying a piezoelectric device, combination, or apparatus to a thing, the applicator including: a body, at least one piezoelectric apparatus in or on the body, electrically conductive material connected to the piezoelectric apparatus, the electrically conductive material in one aspect being nanomaterial. In one aspect, the nanomaterial is carbon nanomaterial and, in one aspect, the carbon nanomaterial is carbon nanotubes. In certain aspects, the detectable material, in any embodiment herein (including, but not limited to, the material DM, FIG. 1) is such nanomaterial, whether electrically conductive or not.

In certain aspects, the electrically conductive material or electrical conductor of embodiments of the present invention is electrically conductive nanomaterial that includes any known nanomaterial which can conduct electricity including, but not limited to, electrically conductive nanotubes, nanorods, nanowires, nanoparticles, nanostructures, nanofibers, nanofabric, nanocylinders, nanotextiles, nanographene, nanographene ribbons, transformed nanomaterials, functionalized nanomaterial, metallized nanomaterial, and/or carbon nanomaterials, e.g., but not limited to, carbon nanotubes, and/or electrically conductive nanotubes including single walled nanotubes, multi-walled nanotubes, functionalized nanotubes and/or metallized nanotubes. In certain aspects, the detectable material, in any embodiment herein (including, but not limited to, the material DM, FIG. 1) is such nanomaterial, whether electrically conductive or not.

Certain embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated.

There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention and its diverse embodiments recognize and address the long-felt needs and provides a solution to problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of certain preferred embodiments, given for the purpose of disclosure, when taken in conjunction with the accompanying drawings. The detail in these descriptions is not intended to thwart this patent's object to claim this invention no matter how others may later disguise it by variations in form, changes, or additions of further improvements.

It will be understood that the various embodiments of the present invention may include one, some, or any possible combination of the disclosed, described, and/or enumerated features, aspects, and/or improvements and/or technical advantages and/or elements in claims to this invention.

BRIEF DESCRIPTION OF THE SEVERAL VIEWS OF THE DRAWINGS

A more particular description of embodiments of the invention briefly summarized above may be had by references to the embodiments which are shown in the drawings which form a part of this specification.

These drawings illustrate embodiments preferred at the time of filing for this patent and are not to be used to improperly limit the scope of the invention which may have other equally effective or legally equivalent embodiments. In the appended figures, similar components and/or features may have the same numerical reference label.

Various components of the same type may be distinguished by following the reference label by a letter that distinguishes among the similar components and/or features.

If only the first numerical reference label is used in the specification, the description is applicable to any one of the similar components and/or features having the same first numerical reference label irrespective of the letter suffix.

Figure 1:
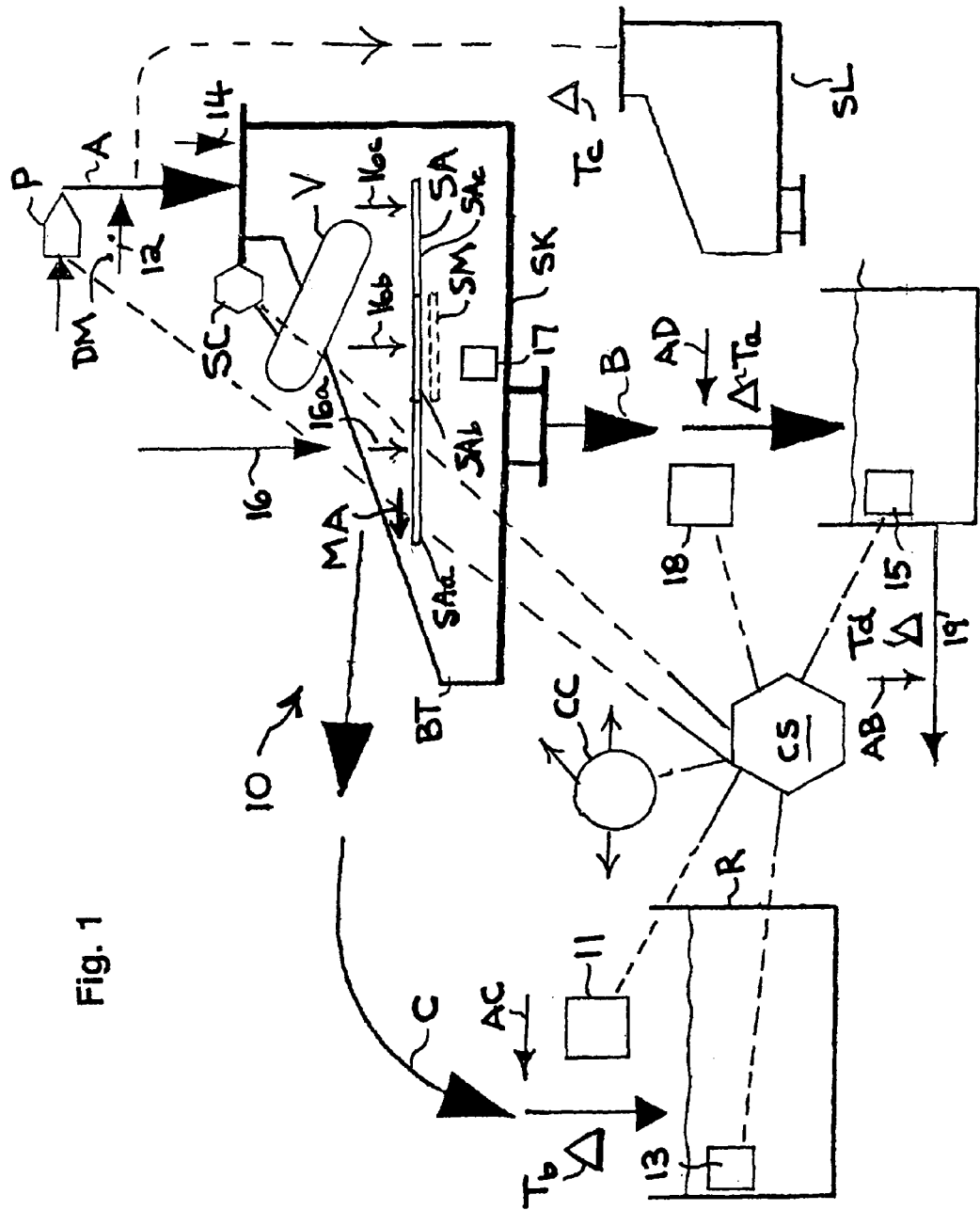

FIG. 1 is a schematic view of a system according to the present invention.

FIG. 1A is a schematic view of a system according to the present invention.

FIG. 2 is a schematic view of a system according to the present invention.

FIG. 3 is a schematic view of a system according to the present invention.

FIG. 4 is a schematic view of a system according to the present invention.

Figure 5:
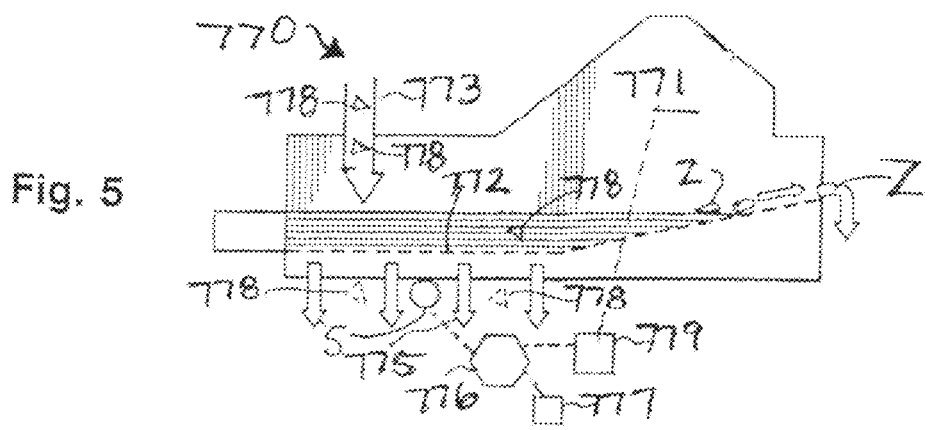

FIG. 5 is a schematic view of a system according to the present invention.

Figure 6:
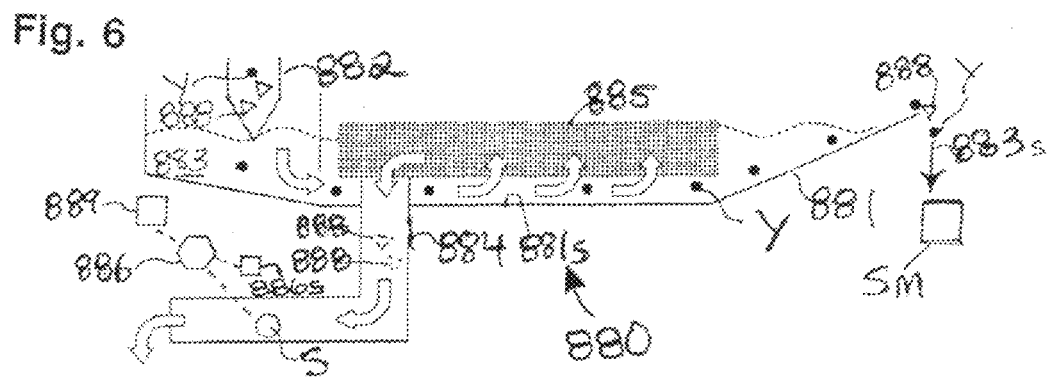

FIG. 6 is a schematic view of a system according to the present invention.

Figure 7:
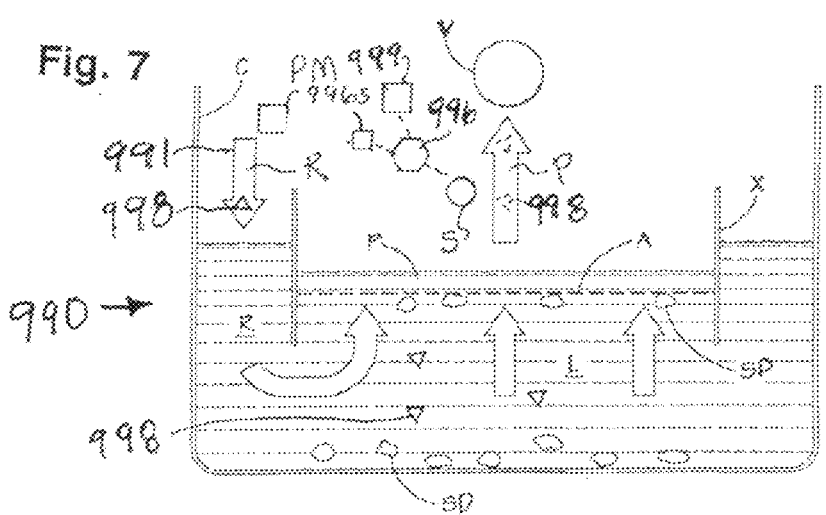

FIG. 7 is a schematic view of a system according to the present invention.

Figure 8A:
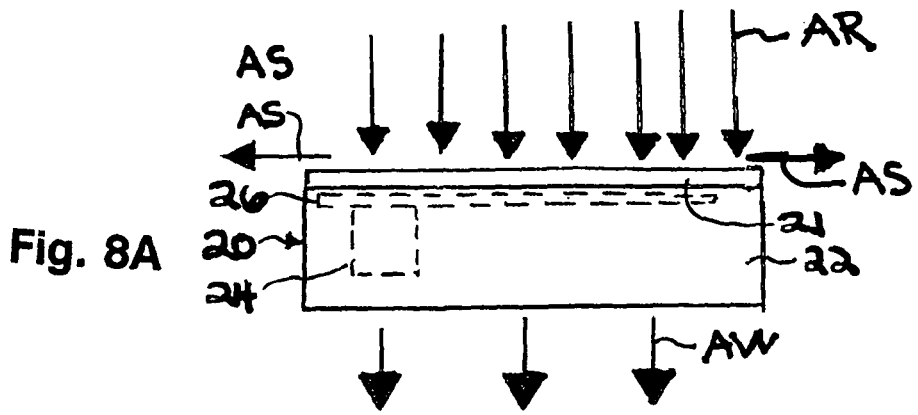

FIG. 8A is a schematic view of a screen according to the present invention.

Figure 8B:
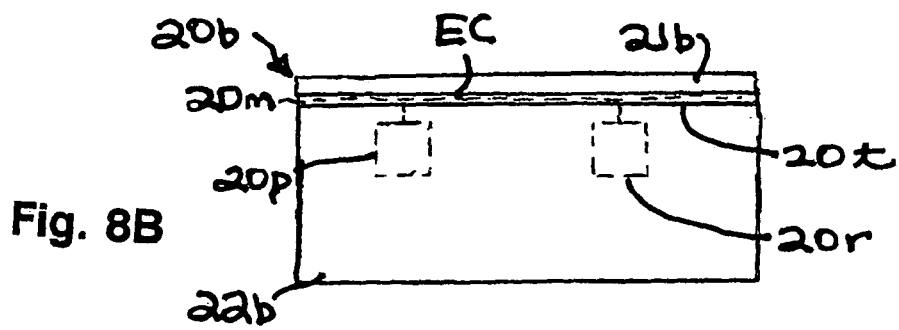

FIG. 8B is a schematic view of a screen according to the present invention.

Figure 8C:
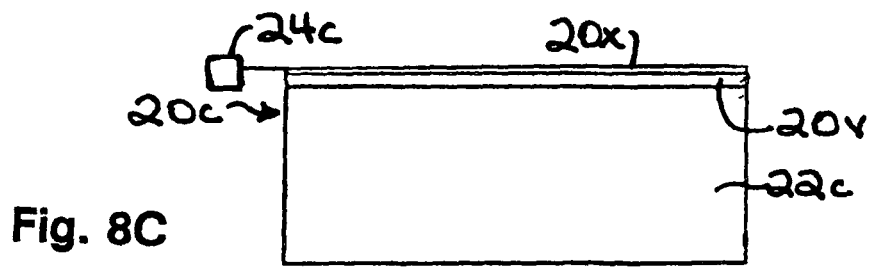

FIG. 8C is a schematic view of a screen according to the present invention.

Figure 8D:
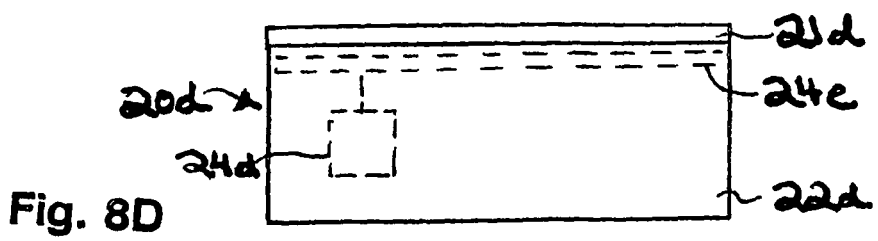

FIG. 8D is a schematic view of a screen according to the present invention.

Figure 9A:
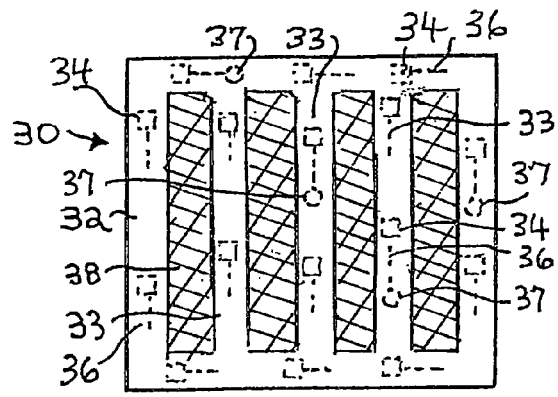

FIG. 9A is a bottom view of a screen according to the present invention.

Figure 9B:
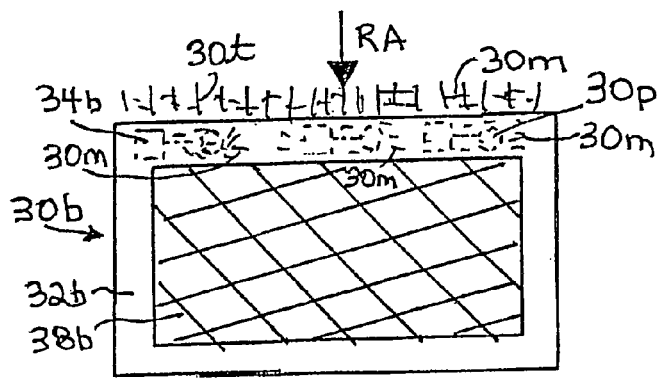

FIG. 9B is a top view of a system according to the present invention.

Figure 10:
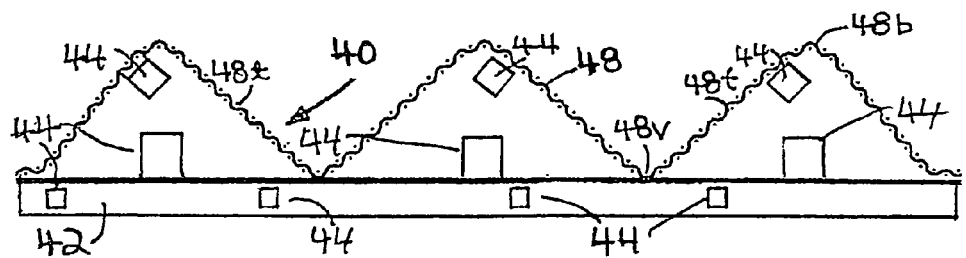

FIG. 10 is an end view of a screen according to the present invention.

Figure 11A:
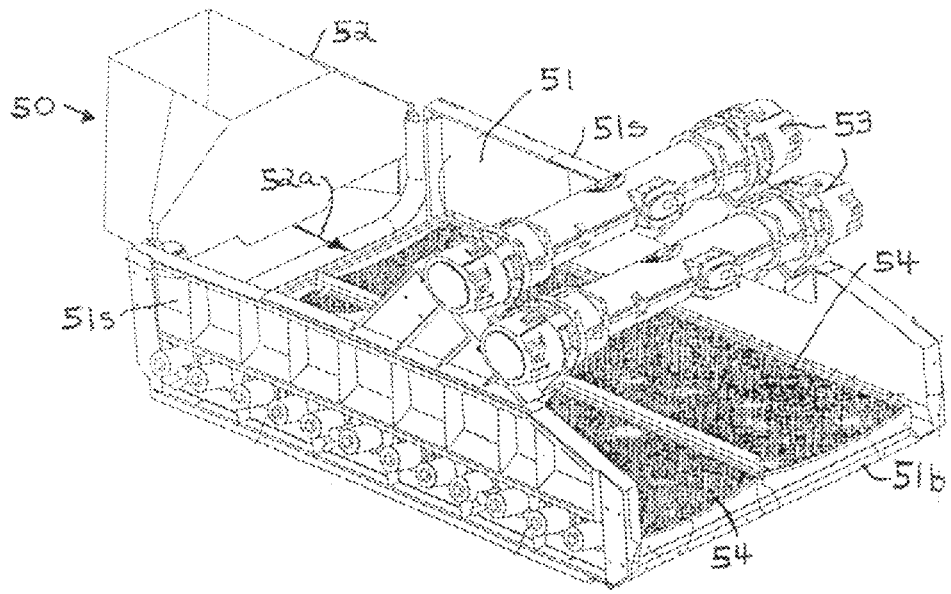

FIG. 11A is a perspective view of a shaker system according to the present invention.

Figure 11B:
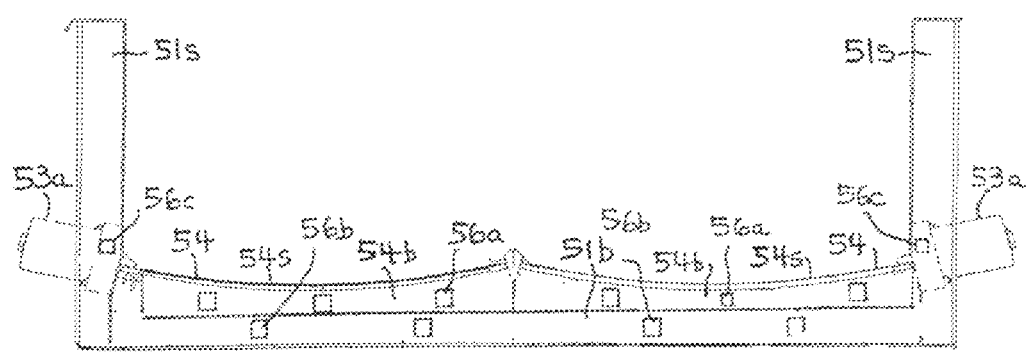

FIG. 11B is an end view of part of the shaker system of FIG. 5B.

Figure 12:
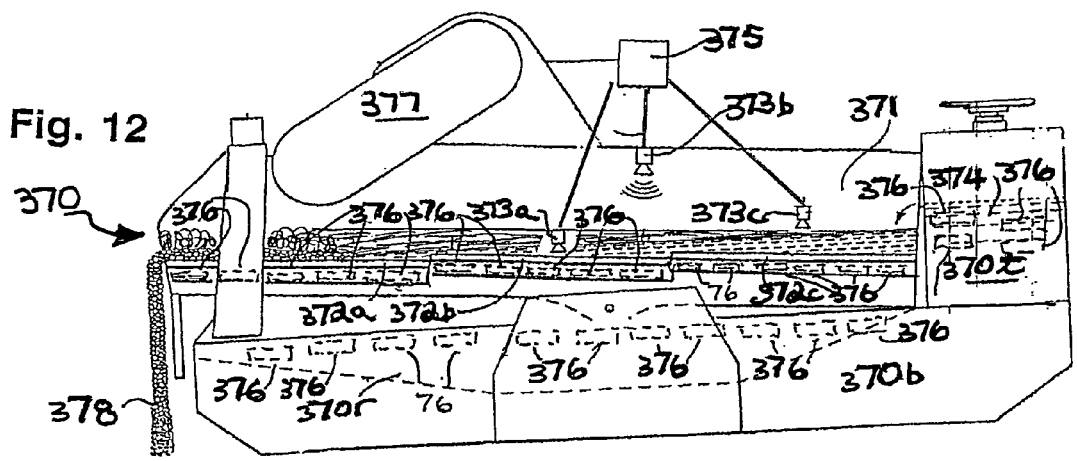

FIG. 12 is a schematic side view of a shaker system according to the present invention.

Figure 13:
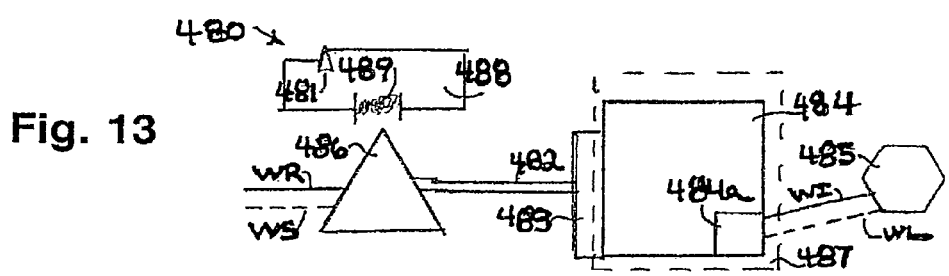

FIG. 13 is a schematic view of a system according to the present invention.

Figure 14A:
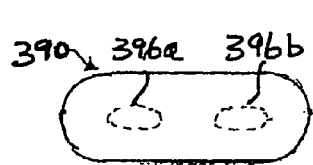

FIG. 14A is a schematic view of a system according to the present invention.

Figure 14B:
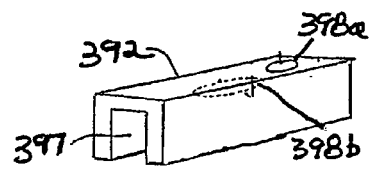

FIG. 14B is a schematic view of a system according to the present invention.

Figure 14C:
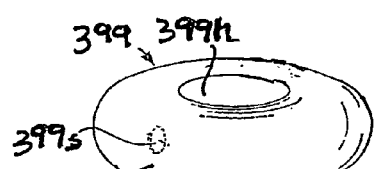

FIG. 14C is a schematic view of a system according to the present invention.

Figure 15A:
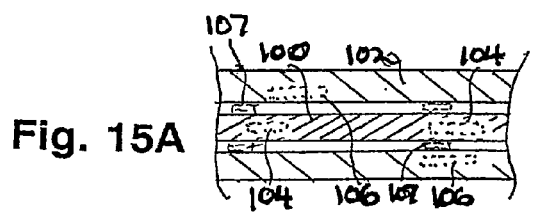

FIG. 15A is a cross-section view of a rotating shaft system according to the present invention.

Figure 15B:
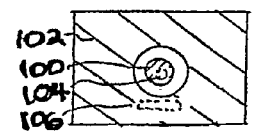

FIG. 15B is a cross-section view of the rotating shaft system of FIG. 10A.

Figure 16:
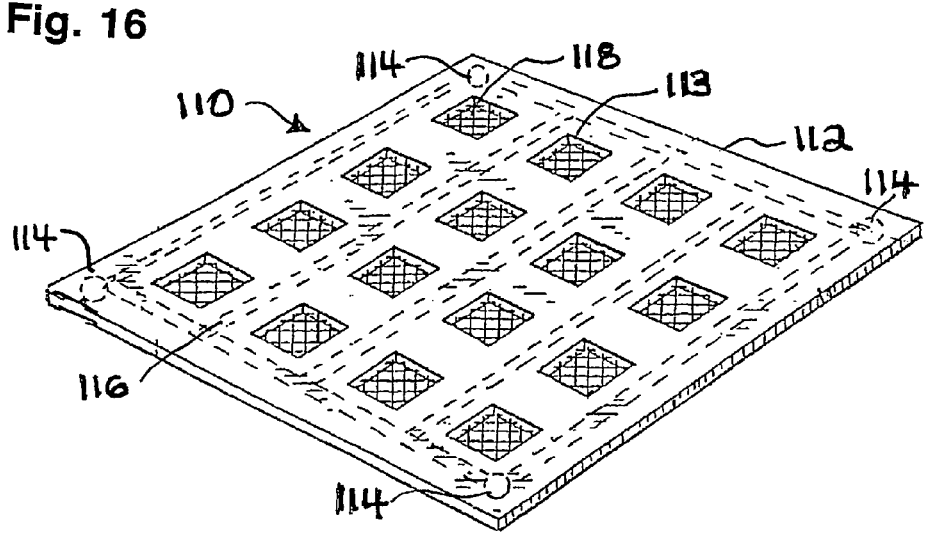

FIG. 16 is a perspective view of a screen according to the present invention.

Figure 17:
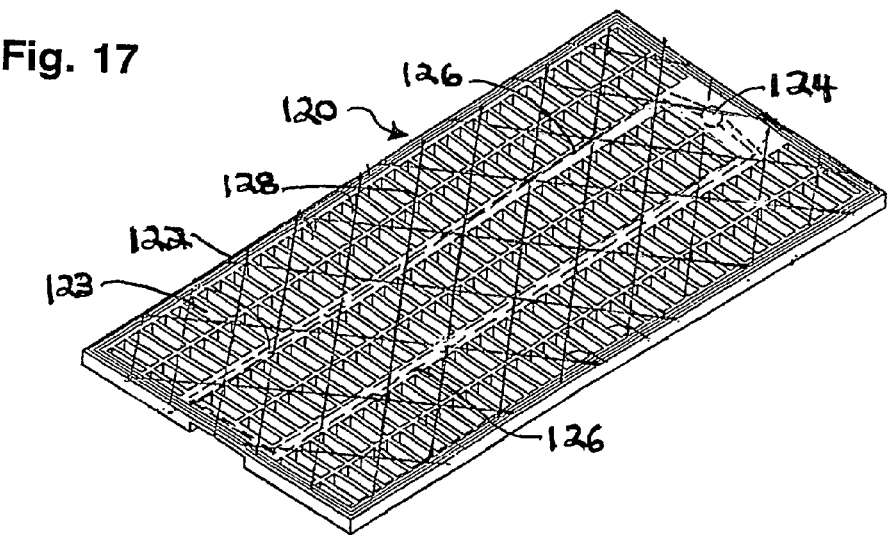

FIG. 17 is a perspective view of a screen according to the present invention.

FIG. 18A is a perspective view of a shaker system according to the present invention.

FIG. 18B is an end view of part of the system of FIG. 18A.

FIG. 18C is an end view of a system according to the present invention.

FIG. 18D is a perspective view of a material introduction strucutre for a system according to the present invention.

Figure 19A:
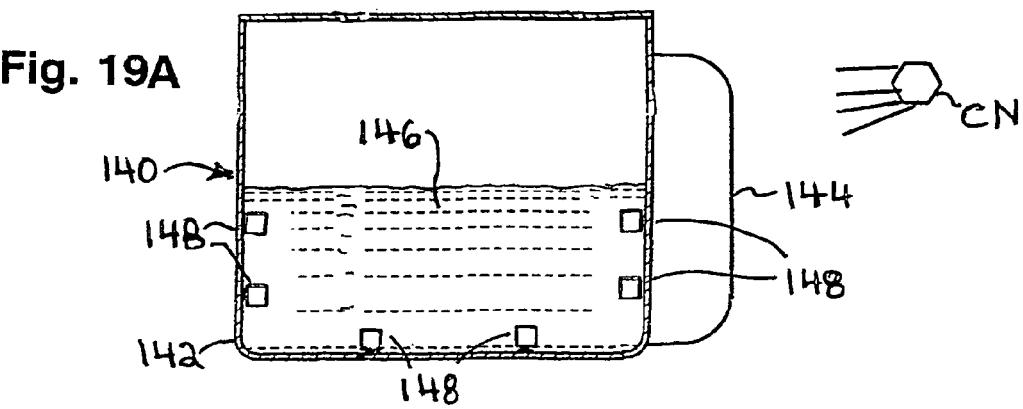

FIG. 19A is a schematic cross-section view of a system according to the present invention.

Figure 19B:
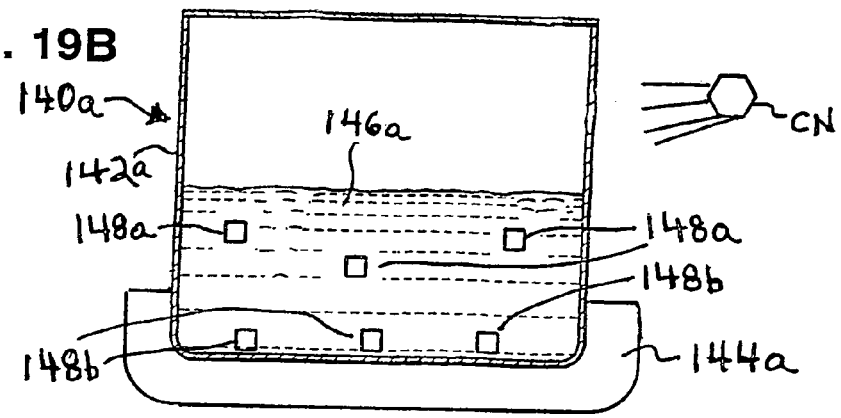

FIG. 19B is a schematic cross-section view of a system according to the present invention.

Figure 19C:
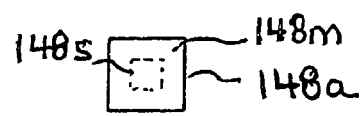

FIG. 19C is a side view of a system according to the present invention.

Figure 19D:
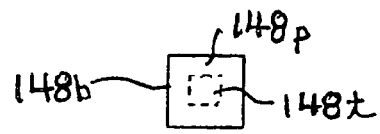

FIG. 19D is a side view of a system according to the present invention.

Figure 20:
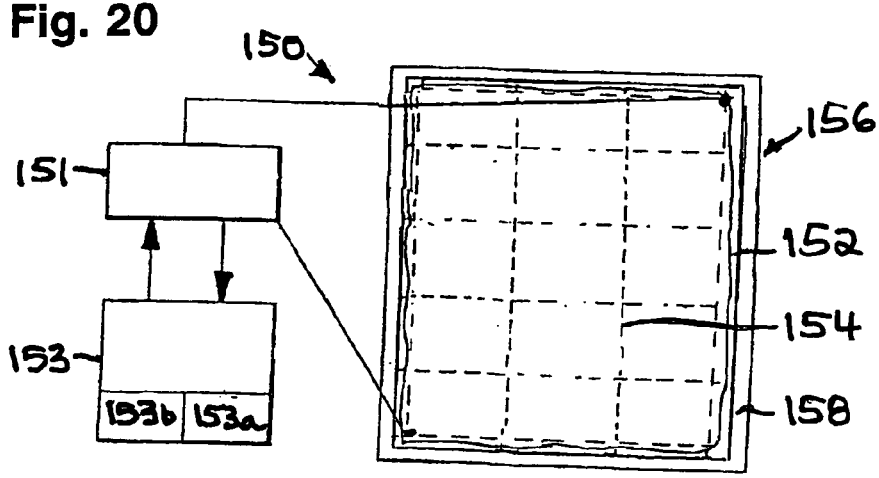

FIG. 20 is a top schematic view of a screen system according to the present invention.

Figure 21:
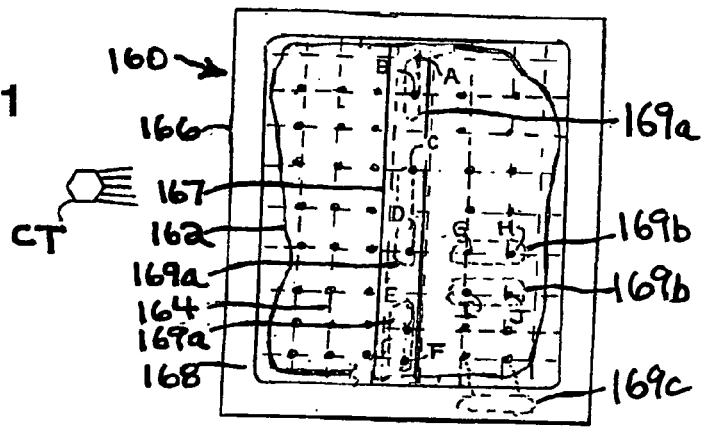

FIG. 21 is a top schematic view of a system according to the present invention.

Figure 22:
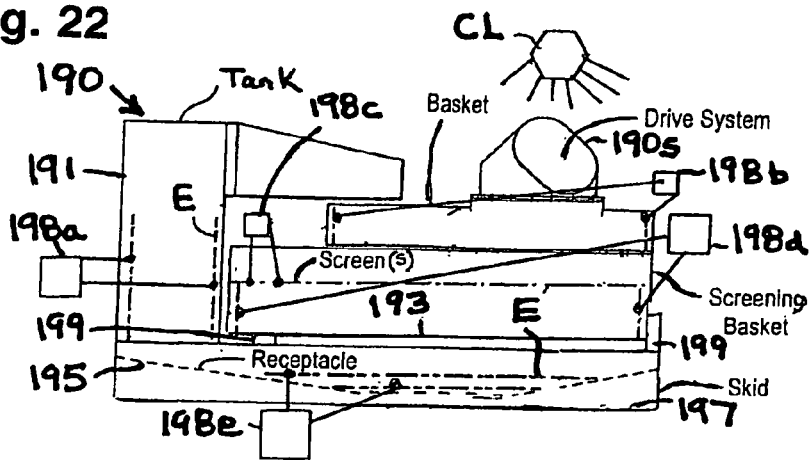

FIG. 22 is a side schematic cross-section view of a vibratory separator system according to the present invention.

FIG. 23 is a side schematic cross-section view of a vibratory separator system according to the present invention.

FIG. 24A is a perspective view of a vibratory separator system according to the present invention.

FIG. 24B is a side cross-section view of part of the system of FIG. 24A.

Certain embodiments of the invention are shown in the above-identified figures and described in detail below. Various aspects and features of embodiments of the invention are described below.

Any combination of aspects and/or features described below can be used except where such aspects and/or features are mutually exclusive.

It should be understood that the appended drawings and description herein are of certain embodiments and are not intended to limit the invention.

On the contrary, the intention is to cover all modifications, equivalents and alternatives falling within the spirit and scope of the invention as defined by the appended claims.

In showing and describing these embodiments, like or identical reference numerals are used to identify common or similar elements. The figures are not necessarily to scale and certain features and certain views of the figures may be shown exaggerated in scale or in schematic in the interest of clarity and conciseness.

As used herein and throughout all the various portions (and headings) of this patent, the terms "invention", "present invention" and variations thereof mean one or more embodiments, and are not intended to mean the claimed invention of any particular embodiment.

Accordingly, the subject or topic of each such reference is not automatically or necessarily part of, or required by, any particular embodiment.

So long as they are not mutually exclusive or contradictory any aspect or feature or combination of aspects or features of any embodiment disclosed herein may be used in any other embodiment disclosed herein. The present invention includes a variety of aspects, which may be combined in different ways.

The following descriptions are provided to list elements and describe some of the embodiments of the present invention, including those preferred at the time of filing for this patent.

These elements are listed with initial embodiments, however it should be understood that they may be combined in any manner and in any number to create additional embodiments. The variously described examples and preferred embodiments should not be construed to limit the present invention to only the explicitly described systems, techniques, methods and applications.

Further, this description should further be understood to support and encompass descriptions and claims of all the various embodiments, systems, techniques, methods, devices, and applications with any number of the disclosed elements, with each element alone, and also with any and all various possible permutations and combinations of all elements in this or any subsequent application.

The ensuing description provides exemplary embodiments only, and is not intended to limit the scope, applicability or configuration of the disclosure.

Rather, the ensuing description of the exemplary embodiments will provide those skilled in the art with an enabling description for implementing one or more exemplary embodiments.

Various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details.

For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Although an operation may be described as a sequential process, many of the operations can be performed in parallel or concurrently. In addition, the order of the operations may be re-arranged.

A process may be terminated when its operations are completed, but could have additional steps not discussed or included in a figure.

Furthermore, not all operations in any particularly described process may occur in all embodiments.

Embodiments of the invention may be implemented, at least in part, either manually or automatically. Manual or automatic implementations may be executed, or at least assisted, through the use of machines, hardware, software, firmware, middleware, microcode, hardware description languages, or any combination thereof.

When implemented in software, firmware, middleware or microcode, the program code or code segments to perform the necessary tasks may be stored in a machine readable medium. A processor(s) may perform the necessary tasks.

DETAILED DESCRIPTION OF THE INVENTION

FIG. 1 shows a system 10 according to the present invention which has vibratory separator apparatus which, in this case includes a shale shaker SK which receives drilling fluid with solids therein pumped from a wellbore (not shown) by a pump system P in a stream A. The shale shaker SK has screen apparatus SA which includes multiple screens SAa, SAb and Sac. As shown, the screens are generally at a similar level; but, optionally, one or more screens may be at different levels, e.g., as shown by the screen SM shown in dotted line.

Vibratory apparatus V vibrates a structure, housing, or basket BT in which the screens are mounted. Material separated from the stream MA (material that does not pass through the screens) flows off the top of the screens in a stream C to a pit or container R. Material flowing through the screens, including drilling fluid, flows down in a stream B to a receptacle or container U.

A control system SC controls the operation of the shaker SK (and it can be any suitable known shaker control system, including, but not limited to, known systems for automatic shaker operation). The control system SC can also control the pump system P. A control system CS controls the system 10 as described in detail below. Optionally, the control system CS also controls a conduit control system CC, described in detail below, and/or the control system SC.

Detectable material DM is fed in a stream 12 into the stream A. Optionally, or instead of the stream 12, detectable material is fed into the shaker SK in a stream 14 that mixes with the material in the stream A in the shaker before the material is fed onto the screens. Optionally, or instead of the stream 12, detectable material is fed in a stream 16 onto the screens. Optionally, a separate stream is fed to each of a plurality of screens; e.g., as shown streams 16a, 16b, and 16c are fed to screens SAa, SAb, and SAc, respectively. Optionally, such a feed stream is fed to screens at different levels in a separator or shaker; and, optionally, a different feed stream can be fed to each screen at each level.

A detector 18 detects detectable material in the stream B flowing down from the shaker SK. A detector 11 detects detectable material in the stream C flowing from the tops of the screens. Optionally, or in addition to the detector 18, a detector 17 in (as shown) or on the shaker SK detects detectable material in the fluid flowing down from the screens.

In one aspect, the stream B flows down into the tank U and a detector 15 in the tank U detects detectable material therein. The detector 15 may be used instead of or in conjunction with the detector 18 and/or the detector 17.

In one aspect, the stream C flows down into the pit R and a detector 13 in the pit R detects detectable material therein. The detector 13 may be used instead of or in conjunction with the detector 11.

Whether or not detectable material from a stream 12 (or a stream 14 or a stream 16) is in the stream B, additional detectable material is, optionally, added to the stream B in a stream AD.

This added detectable material can be the same as, or different from, the detectable material of the stream 12. Any "detectable material" herein may be one of or a combination of any of the detectable materials described herein.

Whether or not detectable material from a stream 12 (or a stream 14 or a stream 16) is in the stream C, additional detectable material is, optionally, added to the stream C in a stream AC. This added detectable material can be the same as, or different from, the detectable material of the stream 12.

Whether or not detectable material from a stream 12 (or a stream 14 or a stream 16) is in the stream 19 that conveys material from the tank U, additional detectable material is, optionally, added to the stream 19 in a stream AB. This added detectable material can be the same as, or different from, the detectable material of the stream 12.

Added detectable material, e.g., in a stream AB, AC, or AD, can be any detectable material disclosed herein used for any purpose or function disclosed herein and/or killing material, e.g., but not limited to a biocide or biocides, (solids, liquid, solution) may be added to any of the streams. Killing material (as solids, liquid, solution or a combination of these), e.g., but not limited to a biocide or biocides, may be added to any of the streams 12, 14, 16, 16a, 16b, 16c, A, B, C and 19.

A combination of detectable material according to the present invention may be the same form of detectable material or it may be different forms of the same detectale material (e.g., and not by way of limitation, materials of different colors which are the same base material; materials of different size which are the same base material); or the different detectable materials may be different materials (e.g., and not by way of limitation, different chemically; material of a specific color with another material of a specific electrical conductivity; light reflective material of multi-micron size and carbon nanotubes; or pieces of plastic material combined with pieces of magnetically-attractive material).

It is within the scope of the present invention to treat a stream of the system 10 before or after a detector detects detectable material in the stream. For example, if detectable material (and/or living things) is detected in one of the streams B, C, or 19, following such detection the stream is treated by a treatment apparatus Ta, Tb, or Td, respectively, which can provide one or a combination of these functions:

heat a stream;
kill living things in a stream, e.g., with heat, electric current, microwaves, and/or killing material;
remove material from a stream;
add killing material to a stream;
remove magnetically attractive material from a stream;
remove magnetically attractive detectable material from a stream;
cool a stream;

apply light and/or laser beam to a stream;
apply radiation (e.g., infrared, microwave, or UV) to a stream; and/or
mix materials in a stream, e.g. for homogeneity.

The control system CS is in communication with the detectors 11, 13, 15, 17, and 18; with the control system SC; with the conduit control system CC; with the pump system P; and with the vibratory apparatus V. Via these connections, the control system CS can shut down the system 10 (e.g., in response to a signal from a detector that indicates screen damage, faulty screen mounting, or inadequate screen sealing) e.g., by stopping the pump system P or by activating the conduit control system CC to stop fluid flow to the system. The conduit control system CC controls all flow lines of the system 10 and includes appropriate and necessary piping, valves, connections, etc. for the various parts and streams of the system.

Optionally, upon shut down of flow to the shaker SK, the control system CS has the stream A diverted to additional equipment or apparatus, e.g., to a tank or to a shaker apparatus SL (as shown by the dotted line from the stream a to the shaker SL). A treatment apparatus Tc can treat the flow stream to the shaker SL.

The control system CS can provide an alarm when any detector detects detectable material. Optionally, such an alarm is provided by a detector itself. With or without shutting down the system and with or without diverting any flow, the control system CS can activate one or all of the treatment apparatuses to treat a stream with which it is associated. In certain particular embodiments, with a separator or shaker with multiple separating elements or screens, the control system CS can shut down flow to a particular screen or screens so that operation can continue, e.g., when detection of detectable material indicates a damaged or worn screen, or poor screen mounting or sealing. Optionally, the control system CS can determine, from signals from detectors, that, although the shaker is not operating optimally, it is operating within an acceptable range; but a notification is provided that only a predicted amount of further acceptable operation is possible.

A control system CS may be used with any separator or shaker system according to the present invention, including, but not limited to, the systems of FIGS. 1-4.

FIG. 1A illustrates a method according to the present invention for testing the efficiency of a separator 61 which separates solids X of a particular size from an input stream 62 that includes solids X. A thing or things 68 is added to the flow 62. The thing(s) are of the same size (e.g., of the same largest dimension) as the solids X so that, if the separator 61 is operating effectively, the thing(s) 68 is/are separated from the flow 62 and is/are discharged with the separated solids X in a stream 64. However, if the separator 61, for whatever reason, allows the thing(s) 68 to pass through and to be discharged in a stream 63, this provides an indication that the separator is not working as desired (the indication provided via monitoring electric current level and/or with ultraviolet light). An apparatus S detects the presence of the things(s) 68 in the stream 63. Optionally the things 68 are detectable material. Optionally killing material KM is added to the stream 62, the stream 63, or both.

The apparatus S can then communicate with a control system 66 (on-site and/or remote) with information about the output stream and, optionally, the control system 66 can activate an alarm 67 and/or can alert and/or inactivate a system 69 which controls the input stream 62 and can alter it or stop it. The separator 61 can be, e.g. and not by way of limitation, any known apparatus, filter, screen, centrifuge, cyclone, solids control apparatus, or hydrocyclone and can include any filter media, screening material, filter, mesh, etc.

In one particular aspect, the apparatus S senses the level of electric current across the stream 63 when no thing(s) are present, providing and/or remembering this typical current level and then, following the introduction of the thing(s) 68 into the stream 62, the apparatus S continues to monitor the current level. A change in the current level from the typical level (the level before the introduction of the things 68) can indicate something wrong with the separator, the items an/or apparatus used to separate out solids of a particular size and/or wear or damage to such items or apparatuses.

A treatment apparatus as any in FIG. 1 may be used with any stream shown in FIG. 1A (and also with any stream in any embodiment hereof and in any stream or streams of FIGS. 2-4).

The thing or things used in the system of FIG. 1A may be any detectable material disclosed herein and the apparatus S may be any detector disclosed herein (and this is true also for any stream of any embodiment hereof and any stream or streams of the systems of FIGS. 2-4).

In certain aspects of the present invention, the thing or thing according to the present invention whose size is known and which is used in checking the efficiency and/or operation of an apparatus and/or monitoring and/or inspecting a filter, screen, etc. is a thing that fluoresces, glows or changes color, e.g., in response to light, to a laser bean, or in response to ultraviolet radiation ("ultraviolet light"). Any apparatus S in any of the drawing figures may contain a source (e.g. a "light" or "lamp"), e.g., of ultraviolet light, which is directed to a stream of material that includes things(s) that respond to light, in some cases providing a visual indication of the presence to the thing(s) and/or glowing, fluorescing, and/or changing color that can be sensed by a sensor in or associated with the apparatus (e.g., an apparatus S). Sensing of the material responding to the ultraviolet light can, e.g., provide and indication that thing(s) according to the present invention have passed through a screen etc, providing an indication of wear, damage, and/or misalignment or poor sealing. In one particular aspect, the apparatus S of the system and method illustrated in FIG. 1 optionally includes a source G of ultraviolet radiation and a sensor H for sensing a material's response to the ultraviolet radiation. Any apparatus S in any of the other methods disclosed herein according to the present invention can have such a source and such a sensor or such sources and such sensors. Methods as described above are referred to as "ultraviolet methods" according to the present invention.

In certain particular aspects in a method according to the present invention that uses radiation or light, e.g. but not limited to, ultraviolet light, as described herein, the "thing" or "things" that respond to the light are solids with material that "lights up" visually or "fluoresces" when subjected to light or ultraviolet light; e.g., but not limited to, phosphors, phosphorescent coating, fluorescent dyes, and other materials that convert ultraviolet radiation to visible light. In one particular aspect, an additive for drilling fluid or "mud" has added to it and/or coated onto it such ultraviolet-light-responsive material. In one particular aspect, a proppant has such material incorporated therein and/or added thereon and/or coated thereon.

In one aspect a sensor H senses a level of fluorescence for a stream into which no thing or things according to the present invention have been added (i.e., no thing or thing that responds to ultraviolet light). A typical level may be zero or there may be something already in the stream that does fluoresces to some degree. The apparatus S stores information (and/or transmits it) of this typical level; and then, following the introduction of the thing(s) into the stream, the apparatus S continues to monitor the fluorescence level. A change in the level from the typical level (before the introduction of the things) can indicate something wrong with the separator, the items and/or apparatus used to separate out solids of a particular size and/or wear or damage to such items or apparatuses.

FIG. 2 illustrates a method 70 according to the present invention for testing the effectiveness of screens used in vibratory separators to screen out solids from an initial flow stream. An initial feed stream 73 is fed to a vibratory separator 71 that has a screen (or screens) 72. The screen(s) 72, when operating correctly and when undamaged, screen out solids Z from the stream 73. The solids Z are of a known size (largest dimension) and the screen(s) is chosen with mesh that will screen out solids of this size. Thing(s) 78 of the same largest dimension as the solids Z is/are added to the stream 73. If the screen(s) 72 are effective, the thing(s) 78 will be screened out and will flow with the solids Z off the top of the screen(s) 72 to a discharge area. If the screen(s) 72 are not effective, (e.g., the screen material is torn or is of the incorrect mesh size or pattern, or if the screen is not correctly mounted to the vibratory separator or not sealingly mounted thereto), then the thing(s) 78 will pass through or by the screen(s) 72 and flow away in a stream 75 (four down pointing arrows below separator 71; things 78 that have passed through screen 72 shown in dotted lines).

An apparatus S detects the presence of the thing(s) 78 in the stream 75. The apparatus S can then communicate with a control system 76 (on-site and/or remote) which in turn can activate an alarm 77 and/or can alert and/or inactivate a system 79 which controls the vibratory separator 71 and/or controls the input stream 73 and can alter it or stop it.

As is true for the methods shown in FIG. 3 and FIG. 4, the method shown in FIG. 2 can also include the apparatus of FIG. 1A with the source(s) G and sensor(s) H and the method of FIG. 2 (as can be the methods of FIGS. 3, 4) can be light methods, e.g., but not limited to, "ultraviolet methods" according to the present invention.

In one particular aspect the stream 73 is a stream of drilling fluid or mud that contains solids (e.g., and not by way of limitation debris, drilled cuttings, and/or drilled solids) which are to be screened out of the fluid by known screen(s) often called "shale shaker screens" with a vibratory separator often called a "shale shaker." The screen(s) 72 may be any known shale shaker screen and the separator 71 may be any known shale shaker. Using a plurality of apparatuses S (and this is true for the system and methods of FIGS. 6, 8 and 9) the location of a tear in a screen or the location of a poor sealing area for screen mounting can be indicated by the flow in that area containing thing(s) (like the things 68 or 78) detected by an apparatus S whose location is known. The things 68, 78, 88 and 98 are to be understood, in certain aspects, to include the things described above that fluoresce in response to UV radiation.

Referring now to FIG. 3, in a method 80 according to the present invention, solids-laden fluid, drilling fluid, or drilling mud in an initial stream 82 is introduced into a pool 83 in an upflow separator 81, and the stream 82 is forced up to a vibrating screen 85 that screens out pieces of solids Y of a particular known size (i.e., the fluid flows up to and through the screen 85, but the solids Y do not flow through the screen 85). Fluid free of the solids Y flow via conduit(s), pipe work or channels 84 to containers, e.g., reservoirs or tanks, for subsequent re-use. The cleaned fluid (e.g., but not limited to, drilling mud) may either exit the separator 81 from the sides or bottom thereof. The solids Y fall under gravity to a lower surface 81s, from which they are conveyed, e.g. by pumping or via a moving belt. The solids Y may be wet with fluid and may be sent in a stream 83s to another system SM, e.g., a screw press, centrifugal device or shaker to further recover fluid, e.g. drilling fluid or mud.

Thing(s) 88 of the same largest dimension as the solids Y is/are added to the stream 82. If the screen 85 is effective, the thing(s) 88 will be screened out and will flow with the solids Y from the screen 85. If the screen 85 is not effective, (e.g., the screen material is torn or is of the incorrect mesh size or pattern, or if the screen is not correctly mounted to the vibratory separator or not sealingly mounted thereto), then the thing(s) 88 will pass through or by the screen 85 and flow away in the stream 84 (things 88 shown in dotted line in stream 84). Apparatuses S detect the presence of the thing(s) 88 in the stream 84. The apparatus S can then communicate with a control system 86 (on-site and/or remote) which in turn can activate an alarm 86s and/or can alert and/or inactivate a system 89 which controls the separator 81 and/or controls the input stream 82 and can alter it or stop it.

FIG. 4 illustrates a method 90 according to the present invention in which an initial stream 91 flows into a container C. The stream 91 contains material R, e.g. material including liquid L and solids S. Optionally, the stream 91 is pumped with a pump PM. The material R flows up to a screen apparatus A which is mounted in a basket or box X. Part P of the material, e.g. liquid or liquid plus some solids which are of such a size that they pass through the screen apparatus A and flow up through the screen apparatus A. The part P is removed from the system by removal apparatus V (e.g. vacuum or pump apparatus). The screen apparatus A is sized to screen out solids of the size of solids Z and part of the material R, e.g. solids S and agglomerations or masses of solids.

The solids Z either settle down in the container C without contacting the screen apparatus A or, upon being prevented from further upward flow by the screen apparatus A and/or by material already adjacent the screen apparatus A, fall downwardly in the container C. It is within the scope of the present invention for the screen apparatus A to be any suitable known screen or screen assembly used for vibratory separators or shale shakers. In one particular aspect the material R is drilling fluid or mud with drilling fluid and drilled solids.

Thing(s) 98 of the same largest dimension as the solids Z is/are added to the stream 91. If the screen apparatus A is effective, the thing(s) 98 will not flow therethrough and will flow with the solids Z away from the screen apparatus A. If the screen apparatus A is not effective, (e.g., the screen material is torn or is of the incorrect mesh size or pattern, or if the screen is not correctly mounted or not sealingly mounted thereto), then the thing(s) 98 will pass through or by the screen apparatus A and flow away with the part P (things 98 shown in dotted lines). Apparatuses S detect the presence of the thing(s) 98 in the part P. The apparatuses S can then communicate with a control system 96 (on-site and/or remote) which in turn can activate an alarm 96s and/or can alert and/or inactivate a system 99 which controls the overall system and each component and/or controls the input stream 91 and can alter it or stop it.

Sequential detection of detectable thing(s) can indicate that a flow path within a separator or shaker is clear. Cessation of detection at any particular point can indicate a blockage at that point.

Fluid flow rate through a separator or shaker can also be determined using the thing(s) and the apparatuses S. The apparatuses S are in communication with a control system (not shown) like any disclosed herein. Also, the method can disclose the location of an amount of fluid within a separator or shaker at any given time; its temperature; the flow rate and/or pressure at its location; and the pH.

Using any suitable UV source, any ultraviolet system and/or method according to the present invention may be used to sterilize fluid, a stream, and/or drilling fluid.

FIG. 5 illustrates a method 770 according to the present invention for testing the effectiveness of screens used in vibratory separators to screen out solids from an initial flow stream. An initial feed stream 773 is fed to a vibratory separator 771 that has a screen (or screens) 772. The screen(s) 772, when operating correctly and when undamaged, screen out solids Z from the stream 773. The solids Z are of a known size (largest dimension) and the screen(s) is chosen with mesh that will screen out solids of this size. McNano device(s) 778 of the same largest dimension as the solids Z is/are added to the stream 773.

If the screen(s) 772 are effective, the McNano device(s) 778 will be screened out and will flow with the solids Z off the top of the screen(s) 772 to a discharge area. If the screen(s) 772 are not effective, (e.g., the screen material is torn or is of the incorrect mesh size or pattern, or if the screen is not correctly mounted to the vibratory separator or not sealingly mounted thereto), then the McNano device(s) 778 will pass through or by the screen(s) 772 and flow away in a stream 775 (four down pointing arrows below separator 771; McNano devices 778 that have passed through screen 772 shown in dotted lines).

An apparatus S detects the presence of the device(s) 778 in the stream 775. The apparatus S can then communicate with a control system 776 (on-site and/or remote) which in turn can activate an alarm 777 and/or can alert and/or inactivate a system 779 which controls the vibratory separator 771 and/or controls the input stream 773 and can alter it or stop it.

In one particular aspect the stream 773 is a stream of drilling fluid or mud that contains solids (e.g., and not by way of limitation debris, drilled cuttings, and/or drilled solids) which are to be screened out of the fluid by known screen(s) often called "shale shaker screens" with a vibratory separator often called a "shale shaker." The screen(s) 772 may be any known shale shaker screen and the separator 771 may be any known shale shaker. Using a plurality of apparatuses S the location of a tear in a screen or the location of a poor sealing area for screen mounting can be indicated by the flow in that area containing McNano device(s) detected by an apparatus S whose location is known.

Referring now to FIG. 6, in a method 880 according to the present invention, solids-laden fluid, drilling fluid, or drilling mud in an initial stream 882 is introduced into a pool 883 in a separator 881, and the stream 882 is forced up to a vibrating screen 885 that screens out pieces of solids Y of a particular known size (i.e., the fluid flows up to and through the screen 885, but the solids Y do not flow through the screen 885). Fluid free of the solids Y flow via conduit(s), pipe work or channels 884 to containers, e.g., reservoirs or tanks, for subsequent re-use. The cleaned fluid (e.g., but not limited to, drilling mud) may either exit the separator 881 from the sides or bottom thereof. The solids Y fall under gravity to a lower surface 881s, from which they are conveyed, e.g. by pumping or via a moving belt. The solids Y may be wet with fluid and may be sent in a stream 83s to another system SM, e.g., a screw press, centrifugal device or shaker to further recover fluid, e.g. drilling fluid or mud.

McNano device(s) 888 of the same largest dimension as the solids Y is/are added to the stream 882. If the screen 85 is effective, the McNano device(s) 888 will be screened out and will flow with the solids Y from the screen 885. If the screen 885 is not effective, (e.g., the screen material is torn or is of the incorrect mesh size or pattern, or if the screen is not correctly mounted to the vibratory separator or not sealingly mounted thereto), then the McNano device(s) 888 will pass through or by the screen 885 and flow away in the stream 884 (McNano device shown in dotted line in stream 884). Apparatuses S detect the presence of the device(s) 888 in the stream 884. The apparatus S can then communicate with the control system 886 (on-site and/or remote) which in turn can activate an alarm 886s and/or can alert and/or inactivate a system 889 which controls the separator 881 and/or controls the input stream 882 and can alter it or stop it.

FIG. 7 illustrates a method 990 according to the present invention for a separator in which an initial stream 991 flows into a container C. The stream 991 contains material R, e.g. material including liquid L and solids SD. Optionally, the stream 991 is pumped with a pump PM. The material R flows to a screen apparatus A which is mounted in a basket or box X. Part P of the material, e.g. liquid or liquid plus some solids which are of such a size that they pass through the screen apparatus A and flow up through the screen apparatus A. The part P is removed from the system by removal apparatus V (e.g. vacuum or pump apparatus). The screen apparatus A is, sized to screen out solids of the size of solids SD and part of the material R, e.g. solids SD and agglomerations or masses of solids. The solids SD either settle down in the container C without contacting the screen apparatus A or, upon being prevented from further upward flow by the screen apparatus A and/or by material already adjacent the screen apparatus A, fall downwardly in the container C.

It is within the scope of the present invention for the screen apparatus A to be any suitable known screen or screen assembly used for vibratory separators or shale shakers. In one particular aspect the material R is drilling fluid or mud with drilling fluid and drilled solids. Optionally, the screen apparatus A is vibrated.

McNano device(s) 998 of the same largest dimension as the solids S is/are added to the stream 991. If the screen apparatus A is effective, the McNano device(s) 998 will not flow therethrough and will flow with the solids S away from the screen apparatus A. If the screen apparatus A is not effective, (e.g., the screen material is torn or is of the incorrect mesh size or pattern, or if the screen is not correctly mounted or not sealingly mounted thereto), then the McNano device(s) 98 will pass through or by the screen apparatus A and flow away with the part P (McNano devices shown in dotted lines).

Apparatuses S detect the presence of the device(s) 998 in the part P. The apparatuses S can then communicate with a control system 996 (on-site and/or remote) which in turn can activate an alarm 996s and/or can alert and/or inactivate a system 999 which controls the overall system and each component and/or controls the input stream 991 and can alter it or stop it.

"McNano devices" or "McNanos" as mentioned above, e.g., with respect to the systems of FIGS. 5-7, include the things described in the paragraphs that follow.

The present invention, in certain aspects, discloses systems, equipment, and methods in which very small devices, including microdevices, nanodevices, nanorobots, microresonant devices ("MRDs), nanotransmitters, and/or nano RFID devices (nano RFIDs or nanotags)-all such very small devices are referred to herein collectively as McNano devices or McNanos. McNano devices are used, according to the present invention, in a variety of operations and with a variety of equipment. In certain embodiments, at least one, one, or a plurality of such McNano device are used in equipment, systems, and operations in the oil and gas industries, e.g. in rig operations, well formation, well completion, well production, fluid processing, solids control, and testing methods and with equipment used in these methods.

In certain aspects, the McNano device(s) are coated, sheathed, or layered with protective and/or strengthening material, e.g., but not limited to plastic, metal, polytetrafluoroethylene, and/or ballistic material to cope with a wellbore environment (e.g. but not limited to, environments of extreme temperature or environments of corrosive or caustic materials or fluids) in which a McNano device is used (and this can be true for an McNano device disclosed herein and any such device described below on any method according to the present invention).

Certain McNano devices used in equipment and methods according to the present invention are those disclosed in U.S. Pub. No. 2009/0027280 and are small micro-resonant devices (MRDs) that can receive an excitation signal and generate and transmit an emission signal, and can be tracked in an oil and gas industry method or environment, e.g., devices that are on the order of about 5 to 100 microns in diameter or up to about 1000 microns or much smaller, down to about 5 nanometers.

McNano devices can include monolithic MRDs that include an antenna component that receives an excitation signal and transmits an emission signal; and a resonator component that receives an excitation signal and generates a corresponding emission signal; and, optionally an outer coating that envelopes the device and isolates the device from its environment; and which coating, in certain aspects according to the present invention, specifically protect a device from fluids and materials encountered in oil and gas operations, within equipment used in such operations, and within oil and gas wells. These devices can have an overall diameter of less than about 1000 microns, e.g., 100 or 10 microns, and a Q value of greater than about 5, e.g., greater than 10, 50, 100, or much higher, and the emission signal can be (i) a resonant frequency of the device emitted at a delayed time compared to the excitation signal (or at a time after the excitation signal has stopped), (ii) a frequency different than the excitation signal; (iii) a signal at a different polarization than the excitation signal, or (iv) a resonant frequency of the device which upon excitation by an excitation field (e.g., a magnetic field), distorts the applied excitation field.

In such McNano devices, the antenna component and the resonator component can be the same component, i.e., one component that functions as both an antenna and as a resonator. The devices can also be designed such that the resonant frequency is proportional to an applied magnetic field, e.g., by fabricating the resonator of a magnetic metal or alloy to induce magnetic field dependence to the resonant frequency.

In certain embodiments, the invention features McNano devices which are MRDS as in U.S. Pub. No. 2009/0027280 in the form of cylindrical or prismatic length extender bars that include a transducer material, e.g., a piezoelectric or magnetostrictive transducer material, and that have a length of less than about 100 microns and a diameter of less than about 100 microns; and optionally an outer coating that envelopes the device and isolates the device from its environment in a well or in equipment used in oil and gas operations. In certain aspects, these McNanos can resonate at a resonant frequency of greater than about 50 MHz after receiving an excitation signal at the reonant frequency.

An outer layer for such McNano devices can include a hydrophilic material encompassing the device or a hydrophobic material encompassing the device and/or a protective sheath, layer, or coating.

In other embodiments, the McNano devices are in the form of devices that include a hermetically-sealed housing having walls forming an internal chamber; a cantilever arranged within the internal chamber and having a free end and a fixed end connected to a wall of the housing; and an electrode arranged within the internal chamber in parallel and spaced from the cantilever; wherein, in certain aspects, the overall size of the device is no larger than about 1000 microns, e.g., no larger than 100 or 10 microns.

In certain aspects, in a well, near a well, and/or in or near equipment used in well operations, McNano devices are located and/or tracked (e.g. by an "apparatus S) by generating an excitation signal randomly at any location at which they appear or in a target area in which the device might be located; receiving an emission signal from the one or more McNanos, if any, e.g., in a target area; and processing the emission signal to determine the location of the device(s).

In various methods, the McNano devices can have an overall diameter or largest dimension of about 10 microns or less. In embodiments in which the emission signal is a resonant frequency of the device, the device can further include a magnetic material to induce magnetic field dependence to the resonant frequency, and the methods can further include exposing the device or the device in a target area to a magnetic field.

McNano device(s) 98 of the same largest dimension as the solids S is/are added to the stream 91. If the screen apparatus A is effective, the McNano device(s) 98 will not flow therethrough and will flow with the solids S away from the screen apparatus A. If the screen apparatus A is not effective, (e.g., the screen material is torn or is of the incorrect mesh size or pattern, or if the screen is not correctly mounted or not sealingly mounted thereto), then the McNano device(s) 98 will pass through or by the screen apparatus A and flow away with the part P (McNano devices shown in dotted lines). Apparatuses S detect the presence of the device(s) 98 in the part P. The apparatuses S can then communicate with a control system 96(on-site and/or remote) which in turn can activate an alarm 96s and/or can alert and/or inactivate a system 99 which controls the overall system and each component and/or controls the input stream 91 and can alter it or stop it.

McNano devices may have an overall outer diameter or largest dimension of less than about 1000 microns, and can be much smaller, e.g., less than 500, 250, 100, 50, 20, 10, 5, or 1 micron, or even on the nanometer scale, e.g., 500, 250, 200, 100, 50, 25, 10, or 5 nanometers. McNanos can be individual, standalone, monolithic devices, or can be made of a set of or a plurality of McNanos, e.g. nano-resonant devices, that are each on the nanoscale, e.g., in certain aspects, about 500 nanometers or less, e.g., less than 250, 100, 50, 25, 10, or 5 nanometers in size.

The McNano devices can either (i) individually produce a resonant signal, e.g. when detected, or when acting in concert in a particular target location, or a set of McNano devices can produce a collective signal of sufficient power to be detected in the same way that a signal from one device is detected, or (ii) individually do not produce a signal, but assemble, e.g., self-assemble, at a location or at a target location to form a McNano device, e.g. micro-resonant device, to produce a detectable signal or collectively act to produce a detectable signal. Once congregated or self-assembled at a location or at a target location, a set of McNano devices can act like a single device. Alternatively, the McNano devices can each individually produce a detectable signal.

The McNano devices can be designed and fabricated so that their resonant frequency is sensitive to their surrounding temperature, chemistry, pH, thus making them useful as local sensors with detectable readout (e.g. RF readout). McNano devices with metal or with metallic layers can be detected by conventional metal detection devices and apparatuses.

The McNano device(s) can be micron-sized devices that can generate and emit signals at resonant frequencies not present (or at very low levels) in a location, a target location, or in and oil and gas well environment. In certain aspects, these individual devices, e.g., located in a target environment, can be located in three-dimensional space and tracked anywhere in the target environment using conventional methods and apparatuses. If an RF device is used, one or more can be used to locate the presence of the McNano devices and can also determine the 3-D location, e.g., by using three separate RF devices. Alternatively, one can use even a single antenna (RF device) if it is focused and rotated around the target.

In certain aspects, McNano devices are monolithic devices, i.e., they are fabricated entirely on a single silicon chip or substrate. They can also be standalone devices, in that they can operate without the need for any connection to another circuit or device. Their power requirements can be provided from an on-board power source or from detectors used to detect, track and image them. They can be detected individually, or e.g. when they are composed of a set of nano-scale McNano devices, they can be detected when congregated at a location or at a target location within a target environment or area.

In certain embodiments, McNano devices can have a coating, sheath, or layer that insulates them from a fluid, a material, or an environment. The coating can be hermetically sealed to keep its interior free from fluids, e.g., liquids and/or gases in an environment.

Certain McNano devices convert mechanical motion into an electrical signal (as in U.S. Pub. No. 2009/0027280).

A simple tracking device (e.g. an "apparatus S") for tracking McNano devices can have a single send/receive antenna that is focused to a precise point in 3-D space. To create an image of a large object, the antenna is scanned in three dimensions, e.g., in a circular, up/down, and in/out, thus probing the entire 3-D space occupied by the large object. Another device has a ring of antennae, or multiple rings of different diameter, that are scanned in one direction, e.g., up and down, to reconstruct a 3-D location of a McNano. Another device includes a large, but finite, number of antennae that reconstruct the position of Mcnano devices in 3-D space without moving.

McNanos can also sense for pH, specific chemicals, etc. encountered in an oil and gas well.

In one aspect of the invention, a McNano device is a nano radio frequency identification (RFID) device that includes a radio frequency (RF) section configured to send an RF signal and at least one antenna operatively coupled to the RF section for emitting the RF signal, and the nano RFID device is configured to be less than about 150 nanometers in each of width, length and thickness.

In another aspect, a method for using a McNano device that is nano radio frequency identification (RFID) device, the nano RFID device includes a radio frequency (RF) section configured to emit an RF signal and at least one antenna operatively coupled to the RF section to emit the signal, wherein the nano RFID device is configured to be less than about 150 nanometers in each of width, length and thickness, the method including configuring identification data within the nano RFID device that identifies the RFID device and embedding the nano RFID device within an item or composition for tracking the item or composition. Identification data can similarly be configured in other McNanos. A McNano device can be energized and/or interrogated with an RF signal.

The method and device of the invention includes, in certain aspects, providing a nano radio frequency identification (RFID) device (RFID tag) of about 150 nanometers or smaller in dimension. In some embodiments, the RFID device may include semiconductors as small as is 90 nanometers, perhaps with some chips configured and provided at the 65 nanometer, 45 nanometer and/or 30 nanometer size level. The technology for included electrical circuitry in such a McNano or in any other suitable McNano may include CMOS or related technology for low power consumption.

A McNano device for use in methods according to the present invention may include a nano RFID device with a radio frequency circuit (RF) that may be configured to respond to a received RF signal and to provide identifying information of the nano RFID device which may be associated with a composition, item, product, person, or similar object. Optionally, and as is true for any McNano device, in some applications, the nano RF circuit may provide identifying information of the device when not triggered by a received RF signal; and identifying information may be electronically encoded alphanumeric data to uniquely identify the nano-RFID device.

The RF circuit may also be configured with a memory, such as, but not limited to, EEROM or EEPROM, for example, to store other information that may be transmitted along with the identifying information. The nano RFID device may also include antennae that may receive an RF signal and also emit a response signal as generated by an RF circuit. The antennae may be at least one, or two, carbon nano tubes or other nano materials suitable for RF reception and emission such as transmitting an outbound backscatter signal. As is true of any McNano device, a nano RFID device may have a protective layer, sheath, or coating such as a plastic coating, polytetrafluoroethylene coating, or other suitable composition that provides environmental protection for the nano-RFID device. The nano-RFID device may have a size of about 150 nanometers, or smaller, in all dimensions (length, width and thickness).

A McNano device that has an active nano RFID component may include an active nano RFID device and may include a radio frequency circuit (RF) that is configured to receive a RF signal and configured to emit data as initiated by the RF circuit or as initiated by a micro-circuit (e.g., a micro-processor, or the like) that provides additional processing and control capability. The emitted data may include identifying information of the active nano RFID device, which may be associated with a composition, item, product, object, person, or similar object. The identifying information may be electronically encoded alphanumeric data to uniquely identify the nano-RFID device. The active nano device may also be configured with a memory, such as EEROM or EEPROM, for example, to store the identifying data, and/or other information that may be transmitted along with the identifying information.

The McNano device may include (as is true for any Mcnano device) an active nano device and a nano power source such as a nano battery or a power generator, for example. The power source may be fabricated as a nano chemical-battery as is known in the art. The power source may be configured to provide power to an RF circuit of the device, a micro-circuit, and/or memory. The power source may provide sufficient power to cause a stronger response signal, hence greater transmission distances, as compared with a passive nano RFID. Antennae may receive an RF signal and also emit a response signal as generated by the RF circuit that may be initiated by the micro-circuit. The antennae may be at least one, or two or more, carbon nano tubes or other nano materials suitable for RF reception and emission such as transmitting outbound backscatter signal. The RF circuit and the micro-circuit may be combined in some embodiments.

In one method a McNano device in a well operation is a nano-RFID which may be provided, and initialized or configured with identifying data unique to the particular device, and/or unique to an item, composition, person or object associated with the device. This may be (as is true for any McNano device), for example, a serial number, a product code, a name, an encoded identifier, or the like. The device may be embedded in, connected to, or attached to, a composition or material, item, or product or introduced into a fluid or a flow stream. The composition etc. may be tracked and the resulting identification information received by a reception apparatus or system (e.g. an apparatus S) and processed according to an application or system using the device.

In some applications, the identification information within a McNano device (including, but not limited to a nano RFID device) may be duplicated among more than one device, so that more than one device may have the same identification information, or at least a subset of the same information. This capability may be useful in those applications where an associated item might have multiple devices. In such a case, the identification data may be the same identifying data in all the devices in an item or object.

In certain embodiments, a McNano device may contain temperature, pressure, mechanical (e.g., harmonic) electrical, and/or chemical sensors. In one embodiment, the device may also contain a radio transmitter capable of transmitting continuous, interval, or on-demand signals. The transmitter may contain a power supply, such as a battery. Both the transmitter and power supply may be incorporated on a body or on a single chip. The apparatus may contain remotely programmable subdevices or units capable of detecting and analyzing operations and fluid parameters, e.g., but not limited to, temperature, pH, pressure, and electrical and chemical sensors according to time and location.

An apparatuses S in any drawing figure herein may be any detector described herein and may be controlled by a control system as in any figure herein and also can include any known apparatus used to energize, interrogate, control, and/or identify a McNano device. An apparatus S may also be an apparatus S as disclosed in U.S. application Ser. No. 13/373,283. Optionally, and as is true for any piezoelectric apparatus or piezoelectric combination herein in any embodiment of the invention, the piezoelectric apparatus (and/or such an apparatus with a conductor) may be any suitable known piezoelectric generator, piezoelectric electric microgenerator, or any suitable known piezoelectric energy harvesting device or apparatus; including, but not limited to, those disclosed in U.S. Pat. Nos. 6,655,035; 6,771,007; 7,687,977; 7,880,370 and in any of the references cited in these patents. Optionally, the conductor provides electric power to an electrically powered item (e.g., but not limited to, device, machine, electronic device, circuit, chip, or apparatus). Optionally, an electric control apparatus controls and/or limits and/or adjusts and/or regulates the electric power provided by the piezoelectric apparatus to the conductor.

It is within the scope of this invention for the apparatus to be any known control system, transformer, voltage regulator, computerized apparatus, chip or tag. Optionally, an electric control apparatus controls and/or limits and/or adjusts and/or regulates the electric power provided by the piezoelectric apparatus through the conductor to an optional item. It is within the scope of the present invention for the item to be, by way of example and not by way of limitation: a heater; light; alarm; transmitter; sensor; cooler; fan; and electromagnet. Any system or method herein may include such an item and may include any control system or control apparatus disclosed or referred to herein for use therewith. Any system or method disclosed herein may have: an item or items; and/or an apparatus. Optionally, a control system controls the apparatus wirelessly or via a line, with the apparatus including a device for interfacing with and communicating with the control system.

It is within the scope of the present invention for the conductor to be, by way of example and not by way of limitation, any known electrically conductive material, including, but not limited to: wire; adhesive, epoxy, plastic, thermoplastic material, thermosetting material, and glue with conductive material therein; foil; deposited metal; electrically conductive metal; and cable. In one aspect the electrically conductive material is electrically conductive nanomaterial.

In certain particular aspects, the conductor is a line, grid, or pattern of adhesive, glue, plastic, thermoplastic material, thermosetting material, or epoxy with sufficient electrically conductive material or conductive nanomaterial therein that a current is conveyed through the conductor either for resistive heating or for powering an electrically powered device or apparatus, including, but not limited to, an electromagnetic apparatus. Any system or method herein may include such a conductor.

It is within the scope of the present invention for the body of a screen to be, by way of example and not by way of limitation, made of metal, plastic, composite, wood, ceramic, cermet, and fiberglass. In certain aspects, these materials are the nonconducting form of these materials. Any system or method herein may include such a body.

FIG. 8A shows a screen 20 which has a base 22 and a screening member 21. The base 22 may be any known screen base or frame including, but not limited to, any base or frame for any known shale shaker screen. The screening member 21 may be any known screening member or screen, including, but not limited to, any screen, screen layer(s), or mesh for any known shale shaker screen, including, but not limited to, flat screening mesh or layer(s) and non-flat or "3-D" screening layer(s). The screening member 21 may be connected to the base in any known way or manner with any known connector or connective material or adhesive material and/or welding.

Arrows AR indicate the flow of material to the screen 20. Arrows AS indicate material that does not pass through the screen member 21. Arrows AW indicate a component or components of the material that do pass through the screening member 21. In one particular aspect (and as may be the case for any screen herein), the material is solids laden drilling fluid and the material that passes through the screening member 21 is drilling fluid with some or substantially all solids removed from it.

A piezoelectric apparatus 24 in the base 22 provides electric power to a conductor 26 and, optionally, electric power is supplied to an item 28 (like any electrically-powered item disclosed herein; in one aspect an electromagnet device).

FIG. 8B shows a screen 20*b* according to the present invention with a base 22*b* to whose top 20*t* a screen member 21*b* is connected with adhesive material 20*m*. The adhesive material 20*m* has electrically conductive material EC therein to which electric current is applied by a piezoelectric apparatus 20*p*. In one particular aspect, the material EC is electrically conductive nanomaterial. In one particular aspect, the material EC is carbon nanotubes. By this application of electric current, in one aspect, the screen member 21*b* (in whole or in part) is resistively heated by the current from the apparatus 20*p* flowing through the adhesive material 20*m*. In one aspect, the screen member itself is made with electrically conductive material and it too is resistively heated by the current from the apparatus 20*p*. Optionally there are multiple piezoelectric apparatuses in or on a thing or in or on a base or frame of a screen according to the present invention. For example, the screen 20b may have a second piezoelectric apparatus 20r or three, four, five, or any desired plurality of such apparatuses.

FIG. 8C illustrates a screen 20c that has a base or frame 22c on which is a screen member 20v. On top of all or of a portion of the screen member 20v is electrically conductive material 20x to which electric current is applied from a piezoelectric apparatus 24c.

FIG. 8D shows a screen 20d with a base 22d and a screen member 21d. A piezoelectric apparatus 24d applies electric current to an electromagnet apparatus 24e for attracting to the screen member 21d magnetically attractive material in material fed to the screen 20d so that such magnetically attractive material does not pass through the screen member 21d and is held thereon or therein. It is within the scope of the present invention, as is true for any other embodiment herein, for there to be multiple piezoelectric apparatuses 24d and/or multiple electromagnetic apparatuses 24e. The electromagnetic apparatus or apparatuses may be located in or on a base or frame and/or in or on the screen member.

FIG. 9A shows a screen 30 (viewed from the bottom) according to the present invention that has a frame 32 to which is connected a layer 378(or layers) of screening material or mesh. The frame 32 has a plurality of crossmembers 33. To heat substantially all of the layer(s) 38, a plurality of piezoelectric apparatuses 34 are provided within the frame 32 and the crossmembers 33. Each of the apparatuses 34 is connected to an electrical conductor 36 which is resistively heated by the application of electric current from the apparatuses 34. Optionally, some or all of the apparatuses 34 provide electric current to an electromagnetic apparatus 37 so that magnetically attractive material in material being processed by the screen 30 is held to the frame and/or to the crossmembers.

Optionally, not all the frame and/or not all the crossmembers have an electromagnetic apparatus or electromagnetic apparatuses therein or thereon. In one particular aspect, only one side or one end of the frame 32 has an electromagnetic apparatus or apparatuses therein or thereon that is powered by a piezoelectric apparatus or apparatuses. Optionally such a screen may have any desired number of crossmembers. Optionally, one crossmember, the crossmembers, or any number of them as shown in FIG. 9A are deleted.

FIG. 9B shows a screen 30b according to the present invention which has a frame 32b with a screen layer or layers 38b thereon or connected thereto. An arrow RA indicates material that is fed onto the screen 30b and which contains magnetically attractive material 30m. Electromagnetic apparatuses 30p within the frame 32b are powered by electric current from piezoelectric apparatuses 34b that are within the frame 32b. Thus some, a portion, a large portion, or substantially all of the magnetically attractive material 30m within the material 30t fed to the screen 30b is removed by being held to the frame 32b before it can move onto and impact or injure the screen layers 38b.

FIG. 10 shows a cross-section view of a screen 40 that has a base 42 to which is connected a layer 48 (or layers) of non-flat screening material or mesh. The material 48 has alternating tops 48b and valleys 48v with walls 48t. The material 48 is over an opening or openings in the base 42 so that material fed to the screen is screened by the material 48 and certain component(s) of the material pass through the material 48 (and through the base 42) and certain component(s) do not and flow off the top of the material 48. As is true for any screen herein, the base 42 and/or the layer(s) 48 may be a base or layer(s) as used in any known flat, non-flat, or 3-D screen or screen assembly; including, but not limited to, any base or layer disclosed in U.S. Pat. Nos. 7,484,625; 7,264,125; 7,011,218; 5,720,881; 5,783,077; 5,958,236; 5,417,859; 5,417,793; 7,175,027; 6,769,550; 6,662,952 and those disclosed in the references cited in these patents.

One or more piezoelectric apparatuses 44 may be used in or on the base 42 and/or in or on the material 48 to provide electric current: to a conductor or conductors for heating of the material 48 and thus of the material fed to and/or passing through the material 48; and/or to provide electric current to an electrically powered apparatus or apparatuses, which in one aspect, is an electromagnetic apparatus or apparatuses. In one aspect, piezoelectric apparatuses are provided within the base 42 and/or under tops of the material 48. As is true for any piezoelectric apparatus disclosed herein, an apparatus 44 under material 48 may be encased in insulating material 49 as may be a conductor and/or electromagnetic apparatus which is not located within a frame or base.

FIGS. 11A and 11B show a shale shaker 50 according to the present invention which has a basket 51 with side walls 51s and an end 51b. The basket 51 supports screens 54. Material to be treated by the screens is fed from a feed tank 52 and an arrow 52a indicates the direction of feed to the screens. Vibratory apparatuses 53 vibrate the basket 51 which in turn results in vibrating of the screens 54. Optionally, vibrators 53a (FIG. 5B) vibrate the screens 54. In one particular aspect, the present invention provides improvements to the shaker and screens of U.S. Pat. No. 7,578,394, including and improvements herein and/or the improvements of FIGS. 11A and 11B.

Piezoelectric combinations 56b are in or on the end 51b. Piezoelectric combinations 56a are on or mounted beneath the screens 54. Piezoelectric combinations 56c are in or on the basket walls 51s. Any of these piezoelectric combinations may be used for heating or for magnetic removal of material for the feed material. Any of these combinations may be used with a sensor that may be any known sensor used with a shaker or with a shaker screen.

As is true for any embodiment herein, any generating apparatus, electrical current producer, or piezoelectric combination disclosed herein may be controlled by a control system (wired or wirelessly) like any control system disclosed or referred to herein.

Similarly any piezoelectric apparatus or systems in any embodiment of the present invention may be used to produce current to kill living things in material, either by the application of current to living things, by the heating of living things, or both.

FIG. 12 shows a shaker 70 according to the present invention which has a basket 71 vibrated by vibrating apparatus 77. The basket 71 supports three screens 72a, 72b, 72c for treating material 74 introduced onto the screen 72c from a tank 70t on a base 70b.

The shaker 70 and the screens have at least one or a plurality of piezoelectric combinations 76. Optional temperature sensors 73a, 73b, 73c connected to the basket controllably and selectively sense the temperature of material 74. The material 74 may be any material that is screened or is treated by a shaker, including, but not limited to, drilling fluid with solids therein. A sensor or sensors like the sensor 73a may be used above, near, or in the material being treated at any location in the shaker, e.g., in the material 74. The sensor(s) are in communication with a control system 75 which may be any suitable control system or computer(s).

The system 75 controls the sensor(s), receives and processes signals from the sensor(s), and controls the piezoelectric combination(s) 76 in or on the shaker and/or in or on a screen or screens used with the shaker. The control system 75, among other things, turns the piezoelectric combinations 76 on and off; e.g., when a piezoelectric combination 76 includes a conductor which is resistively heated, in order to heat material 74 by heating the screen(s); and/or when a piezoelectric combination 76 includes selectively actuatable electromagnetic apparatus, in order to remove magnetically attractive material from the material 74.

A control system like the system 75 has the components, hardware, media, programming, devices, apparatus, circuits, chip(s), lines, connections, software, and/or electronics to accomplish the stated functions (as is true for any control system for any embodiment herein). Such a control system and/or such piezoelectric combination(s) may be used with any embodiment herein, and, in certain aspects with any shaker and/or any screen herein. The control system 75 may also control the vibratory apparatus 77 and/or the angle of the basket 71; and, in one particular aspect, controls the vibratory apparatus 77 to control the vibration of the piezoelectric apparatuses in each combination to control their current output.

Fluid and/or solid material flowing through the screens flows down into a receptacle 70*r*. Separated material 78 and/or separated component(s) of the originally-introduced material flows off an exit end of the last screen 72*a*.

It is within the scope of the present invention to use one or a plurality of piezoelectric combinations or apparatuses at any location on or in a shaker and/or at any location on or in a screen; and, in one aspect, to heat only a partial area of a screen, an initial material input end of a screen, or to heat substantially all of the screening area of a screen and/or screen frame.

FIG. 13 shows a piezoelectric device 80 according to the present invention which has a piezoelectric apparatus 84 optionally in material 87. The combination 84 produces current, when vibrated, that flows via a conductor 82 to an electrically-powered item 86. Optionally, a control system 85 in communication with an apparatus 84*a*, communicates with and/or controls the apparatus 84. Optionally, the system 85 may also control the item 86 (wired, WR; or wirelessly, WS). Communication between the apparatus 84 and the system 85 is wired (WR) or is done wirelessly (WL).

Optionally, the apparatus 84 may be used with a device 83 which may be any device for transmitting, controlling, changing, or switching the current from the apparatus 84 (e.g., but not limited to, a transformer, transmitter, switch, voltage regulator). Optionally, when the item 86 is an electromagnetic apparatus, the attraction of magnetically attractive material by the item 86 may be indicated by the closing of a circuit 88 when magnetically attractive material 89 is accumulated and the circuit is closed so that an electrical current flow occurs in the circuit 88. This flow may be indicated by a device 81, e.g., an alarm, light, or indicator in the circuit and/or by a signal sent by the device 81. In certain aspects, the item 86 is a cooler, heater, fan, switch, light, alarm, sensor, transmitter, electromagnet, or electronic tag or identifier.

Vibration of the apparatus 84 (and of any piezoelectric system herein) may be effected by a vibratory apparatus (e.g., one which is powered electrically, powered hydraulically, wind powered, solar powered). In one aspect it is vibrated by the vibratory motor or motors of a shale shaker. Vibration of the apparatus 84 (and of any piezoelectric system herein) may also be effected by a part that becomes unbalanced, including, but not limited to a part that becomes unbalanced or whose weight distribution changes, e.g., due to wear or misalignment.

It is within the scope of the present invention to position or mount a piezoelectric apparatus or apparatuses, or a piezoelectric combination or combinations on or within any part of a screen or screen assembly for a vibratory separator or shaker, including, but not limited to, in or on a part of a screen frame, in or on a frame end or side, or in or on a frame crossmember. It is within the scope of the present invention to position or mount a piezoelectric apparatus or apparatuses, or a piezoelectric combination or combinations on or within any part of a mounting structure or basket of a vibratory separator or shaker.

Any piezoelectric apparatus or combination in any embodiment herein may be wrapped in, painted with, covered with, surrounded by, and/or encased in protective material, insulating material, or both, partially or entirely. Also, any piezoelectric device or apparatus alone which is associated with an electrical conductor may be insulated, with or without insulating the electrical conductor. The insulating material may be temperature insulating material or electrical insulating material, or both. For example, a piezoelectric combination used with a vibratory separator's screen assembly is surrounded by insulating material; e.g., when a screen body or screen frame is made of electrically conductive metal, the insulating material may be electrically insulating material.

For example, a piezoelectric combination in a frame crossmember may be encased in insulating material which may be temperature insulating material to insulate the piezoelectric combination from heat of material being treated and/or if the crossmember is electrically conductive metal, the insulating material may be electrically insulating material.

In one aspect, a screen assembly according to the present invention has a lower support plate and one, two, three, four or more screening layers. Optional side hookstrips on sides of the plate facilitate mounting of the screen assembly to certain separators and shakers to a deck or to a mounting structure. On or within the plate is one or are a plurality of piezoelectric devices, apparatuses, combinations. Any entire side area or end area may have a plurality of spaced-apart piezoelectric devices etc. for either heating of that area, removal of magnetically attractive material at that area, or both. In certain particular aspects, the screen assembly is like those of U.S. Pat. No. 4,575,421 or of U.S. Pat. No. 7,571,817; but with one, at least one piezoelectric system (piezoelectric device, piezoelectric apparatus, piezoelectric generator, piezoelectric combination, piezoelectric microgenerator, piezoelectric energy harvesting device or apparatus) or a plurality of them according to the present invention It is within the scope of the present invention to insert into, apply, adhere, or connect a piezoelectric system, to a screen, to a shaker, or to a separator, using a mass, rigid or flexible, which has on it or contains within it the piezoelectric system or systems, with or without insulating material. For example, FIG. 14A shows a mass 90 of material within which is a piezoelectric system 96*a* and/or within which is a piezoelectric system 96*b*. In one aspect, the mass 90 is rigid. Alternatively the system 96*a* is on the mass 90.

In another aspect, the mass 90 is flexible. The mass 90 may be made of flexible material such as, but not limited to, flexible plastic, composite, metal, cloth, fabric, bandage material, elastic material, and tape. The mass 90 can be held in place by wrapping, with connectors, with pins, with hooks, with releasably cooperating fastener material, and with adhesive or glue. The mass 90 may be any suitable material, including, but not limited to, fiberglass, metal, plastic, composite, wood, ceramic, cermet, and polytetrafluoroethylene. Any insulating material described herein may be used with such a mass with a piezoelectric system.

FIG. 14B shows a mass 92 according to the present invention, made, e.g., with the material described above for the mass 90 with or without insulation, with a piezoelectric system 98a thereon and/or with a piezoelectric system 98b therein. The mass 92 has a recess 97 sized, located, and configured for receipt therein of a part or portion of a thing for releasable emplacement of the mass 92 on the thing. Optionally, such a mass, with or without a recess, is placed within a thing, A friction fit can hold the mass 92 in place and/or connectors, welding, fasteners, and/or adhesive may be used to secure the mass in place on a thing. Any tag or energizable identification apparatus in U.S. Pat. No. 7,484,625 may be replaced or used in combination with a piezoelectric system according to the present invention for any purpose or function disclosed herein or in said patent.

FIG. 14C shows a mass 99 according to the present invention which has a body 99b which is generally doughnut-shaped with a central hole 99h. A piezoelectric system 99s is within the body 99b. Such a mass 99 can be placed in or on another thing; and/or the hole 99h can receive part of a thing to facilitate application of the mass 99 to the thing and/or maintenance of the position of the mass 99.

Parts of a vibratory separator or shale shaker may be mommitored using piezoelectric apparatuses as disclosed herein. FIGS. 15A and 15B represent schematically, in cross-section, parts of a separator or shaker; e.g., a rotating shaft 100 rotating within a housing 102 with optional bearings 107. The shaft 100 has piezoelectric system 104 therein (or, optionally thereon) and/or the housing 102 has piezoelectric system 106 therein (or, optionally, thereon). These piezoelectric systems may be used for any function or purpose disclosed herein; including, but not limited to, for indicating vibration of the housing and/or shaft, indicating vibration of the shaft, or both; wear or damage to the housing; wear or damage to a bearing; and/or for heating and/or cooling the housing and/or the shaft. Any control system or control apparatus disclosed or referred to herein may be used with the shaft 100, its piezoelectric systems, the housing 102, and/or its piezoelectric systems.

FIG. 16 shows a screen 110 according to the present invention which has a body 112 with multiple apertures 113. Each aperture 113 has screening material 118 mounted therein or thereover. The screening material may be a single layer or multiple layers of screening material and/or mesh. Within the body 112 is a grid 116 of electrically conductive material which is connected to piezoelectric generators 114 which provide electric current to the grid 116. Vibration of the body 112 results in electric current produced by the piezoelectric generators 114 being applied to the grid 116, resistively heating the grid 116 and thus heating material on and/or passing through the screen 110. Any one or two of the generators 114 may be deleted or more than four such generators may be used.

It is within the scope of the present invention for the body 112 to be a single integral layer; for it to be any of the multi-layer structures disclosed in U.S. Pat. No. 4,728,422; or any layer, base or frame or part thereof of any known vibratory separator screen or shale shaker screen. In one aspect, the body 112 is made of nonconducting material so that the grid 116 and the piezoelectric generators are encased within and insulated entirely by the body 112. Referring to an embodiment which employs one or more of the layers disclosed in U.S. Pat. No. 4,728,422, a grid like the grid 116 may be present in any layer, in any two layers, in any combination of layers, or in all layers. Also, a single piezoelectric generator 114 may be used for any and all grids; or multiple piezoelectric generators may be used in a single layer or in multiple layers.

In one particular aspect, the grid 116 is made of electrically conductive ink, fluid, adhesive material (e.g., cement, glue, epoxy) which has electrical conductive material therein. In one particualr aspect, the electrically conductvie material is elecrtrically conductive nanomaterial. In one particular aspect, the electrically conductive nanomaterial is carbon nanomaterial. In one particular embodiment, the electrically conductive nanomaterial is carbon nanotubes.

In one aspect the screen 110 is a shale shaker screen and vibration of the shale shaker vibrates the screen 110 which in turn vibrates the piezoelectric generators 114 producing electric current. When this current flows to the grid 116, it is heated and this heat heats the body 112 so that drilling fluid flowing to the screen 110 is heated. Any of the associated items, materials, devices, apparatuses, controllers, and control systems disclosed or referred to herein for use with piezoelectric apparatuses and combinations may be used with the piezoelectric generators 114, as well as any controller or control system for a shale shaker. It is also within the scope of the present invention to use any piezoelectric system or a plurality thereof, with an item such as a vibratory separator, shale shaker, basket, screen support, screen, screens, screen assembly, and/or screen assemblies to apply electric current to one or more of these items during the processing of fluid to kill living things in the fluid; including, but not limited to, killing living things in drilling fluid. Suitable materials are used for these items so that the applied electricity kills the living things but does not flow from the item, short circuit, or cause a shock, damage or fire. For example, a basket and/or other parts of a shaker are made of nonconducting material; or a screen support is made of nonconducting material. Also screens can be mounted with insulators; and/or barriers and structures can be used which electrically isolate fluid into which a current is being applied.

Optionally, the body 112 is made of electrically conductive material and the grid 116 and the piezoelectric generators 114 are insulated within the body 112 so that there is no short circuit with the body 112.

The grid 116 may be applied by any suitable known method. In certain aspects, the grid 114 is applied by any suitable known glue application method including, but not limited to, spraying, pouring, and those disclosed in U.S. Pat. No. 6,736,270 and in the references cited in this patent. In other embodiments, the grid 114 is injected into the body 112. With a body 112 that includes hollow members (e.g., but not limited to, a screen frame or base with hollow ends, hollow sides, and/or hollow crossmembers), the material for the grid 114 may be pumped into the hollow member, poured into them, or injected into them.

FIG. 17 shows a screen 120 according to the present invention which has a frame 122 with multiple apertures 123. The apertures 123 have screening material 128 mounted over them. The screening material may be (as is true for any embodiment of the present invention) a single layer or multiple layers of screening material and/or mesh, flat or non-flat, with layers connected together or not. Within the frame 122 is a pattern 126 of electrically conductive material which is connected to a piezoelectric generator 124 which provides electric current to the pattern 126. Vibration of the frame 122 (e.g., by a shale shaker or vibratory separator) results in electric current produced by the piezoelectric generator 124 being applied to the pattern 126, resistively heating the pattern 126 and thus heating material on and/or passing through the screen 120.

All of the options described above for the screen 110 are available for and may be used with the screen 120. Any screen base, support, or frame or layer disclosed herein (or part thereof) for any embodiment hereof which has one or at least one piezoelectric system apparatus, combination, generator, or energy harvester may be salvaged and re-used after screening material thereon is worn or damaged. In one particular aspect the frame 122 is like the frames disclosed in U.S. Pat. No. 7,753,213 and is made with any of the materials disclosed in this patent.

For any screen or screen assembly according to the present invention which has a piezoelectric device, apparatus, combination or generator, piezoelectric microgenerator, piezoelectric energy harvesting device or apparatus (all collectively referred to as "piezoelectric systems") or a plurality thereof, the level of the electrical current output from such system or systems due to vibration of the screen or screen assembly can be sensed and provided to appropriate analysis apparatuses and/or systems to indicate the level of vibration. This level of vibration can also then be used to indicate: whether or not a vibratory apparatus is operating properly; whether or not there is wear or damage to a vibratory motor, shaft, gear, or associated parts; whether or not there is wear of damage to screening material; whether or not there is wear or damage to a screen support, base, or frame; and/or whether or not a screen or screen assembly is properly mounted and secured in place.

Vibration levels for the following can be determined and stored in appropriate storage media, including but not limited to computer and digital storage media: normal vibratory motor operation and such operation using different motor parameters; using a vibratory separator or shaker with undamaged shafts, parts, bearing, etc; processing fluid or material using a screen or screen assembly with undamaged screening material; using a screen or screen assembly with undamaged support, frame or base; and/or using a screen or screen assembly that is properly mounted and sealed in place. With such baseline data, data obtained during actual operation over time and in real time can be compared to the normal baseline data and any difference can be studied, can be the basis for an alarm or warning, and/or can result in the shut down of the vibratory separator, parts inspection and/or replacement, and/or the changing of operating parameters of the vibratory separator—and these things can be done in real time. Such comparisons can also be the basis for in factory testing of new screens, new parts, new vibratory separators and shale shakers, new motors, and the processing of a variety of materials and fluids.

Over time data can be obtained and maintained for each type of separator or shaker, motor, screen and screen assembly, each type of screening material, and each type of material (e.g., but not limited to drilling fluid) that is processed. Such a database can then be used in testing; in design of new systems, motors, separators, shakers and screens; and in monitoring actual operations.

It is within the scope of the present invention to provide a shale shaker (or vibratory separator) in which living things in drilling fluid can be killed in one or in multiple locations in or adjacent the shale shaker. Such a shale shaker may be used with or without screen(s) that also provide electric current to kill living things; and with multiple screens in one shaker, the screens may all be at substantially the same level or the shaker may have one, two, three, four or more levels or tiers of screen(s).

It is also within the scope of the present invention for a shaker (or vibratory separator) to have a tank, hopper, possum belly, or fluid introduction structure from which material to be treated (e.g., but not limited to, drilling fluid with solids therein and/or living things therein) to be made of electrically insulating material and/or for such tank, etc. to have an interior liner or container that is made from electrically insulating material. It is within the scope of the present invention for s shaker (or vibratory separator) to have a basket or other screen support made from electrically insulating material and/or for such a basket or support to have a liner, interior basket, or interior container made of electrically insulating material. One object of such shakers and parts thereof is to provide a space in which or an area in which living things can be killed by electric current without a short circuit of the current and without current flowing from the shaker or from its screen(s). Electric current can be supplied to a shaker (or vibratory separator) and/or to screen(s) in any way disclosed herein and also can be supplied by an independent electric current source in, on, or adjacent to the shaker (or vibratory separator), including, but not limited to, known electric current sources and also piezoelectric current sources. In certain aspects according to the present invention, a container, receptacle, tank or reservoir not in contact with the shaker (or vibratory separator) receives drilling fluid processed through the screen (s) of a shaker (or vibratory separator). The container etc. has a source or sources of electric current therein, thereon, or adjacent thereto (any source of current disclosed herein) to subject the living things to an electric current to kill the living things within the container, etc.

In certain aspects, the source of electric current for a shale shaker (or vibratory separator), part thereof, a screen, or part thereof, is a piezoelectric system or systems. This system or these systems are vibrated by the vibratory apparatus or apparatuses of the shaker (or separator) producing electric current. The system or systems are designed, chosen, controlled, and/or configured so that sufficient electric current is produced to kill living things in the material processed by the shaker or separator. One killing zone, space or area can be provided, e.g., but not limited to, only in the material introduction structure or only in a receptacle that receives processed material, e.g., but not limited to, processed drilling fluid with living things therein. Alternatively, multiple killing zones, spaces, or areas can be provided.

FIGS. 18A and 18B show a shale shaker 130 that has a base 132, material introduction structure 134, and an exit end 131 for separated material. Material 139 with living things therein is fed to the structure 134 and from there onto screen assemblies 136. In one particular aspect, this material is drilling fluid from a drilled wellbore that has solids therein and living things therein. The living things (as is true for any embodiment herein) may include, but are not limited to, microorganisms, bacteria, viruses, fungi, protests, microbes, aerobic living things, anaerobic living things, algae, and/or spores (and such living things may be in any fluid treated by any method or system herein according to the present invention; and they may be in any fluid treatable with any system or any method according to the present invention, including, but not limited to, drilling fluid, fracturing fluid, fuels, shipboard fuels, ballast liquid, ballast water, metal cutting fluids, milk, water, blood, liquid mediums, and/or plasma). Optionally, the material 139 is also processed with additional screen assemblies (not shown) which may be at different levels. The shaker 130 and the screens 136 are vibrated by vibration apparatuses 130*v*.

Material that does not pass through the screen assemblies 136 moves off the screens at the exit end 131 (e.g., but not limited to, drilled solids, debris, and/or cuttings that are too large to pass through any of the screens). This material may be sent to storage (not shown) or to additional processing equipment APE. Material that passes through the screens (e.g., fluid with living things therein) flows down to a receptacle 135. From the receptacle the material is transmitted (e.g. by gravity flow and/or by pumping) to storage (not shown) or to further processing equipment FPE. As is true for any stream to or from any separator or shaker herein, killing materil KL may be added to the input to the shaker 130 and to either or both of its outputs.

In one aspect, a piezoelectric system 138*i* or a plurality of the systems 138*i* are provided within or on the introduction structure 134. When the shaker 130 is vibrated by the vibratory apparatuses 130*v*, and the introduction structure is vibrated directly or indirectly the system(s) 138*i* produce electric current that kills living things in the material in the structure 134 (this includes material flowing through the structure 134).

In one aspect, a piezoelectric system 138*s* or a plurality of the systems 138*s* are provided within, under and/or on the screens 136*a*-136*c*. When the shaker 130 is vibrated by the vibratory apparatuses 130*v*, the system(s) 138*s* produce electric current that kills living things in the material on or in the screens (this includes material flowing through the screens).

In one aspect, a piezoelectric system 138*e* or a plurality of the systems 138*e* are provided within or on the exit end 131. When the shaker 130 is vibrated by the vibratory apparatuses 130*v*, the system(s) 138*e* produce electric current that kills living things in the material on the exit end 131 (this includes material flowing on the exit end).

In one aspect, a piezoelectric system 138*r* or a plurality of the systems 138*r* are provided within or on the receptacle 135. When the shaker 130 is vibrated by the vibratory apparatuses 130*v*, the system(s) 138*r* produce electric current that kills living things in the receptacle 135 (this includes material flowing through the receptacle).

In one aspect, a piezoelectric system 138*w* or a plurality of the systems 138*w* are provided within or on walls of the base 132 (which, in one aspect, may be walls of a basket mounted in or on the base). When the shaker 130 is vibrated by the vibratory apparatuses 130*v*, the system(s) 138*r* produce electric current that kills living things in the receptacle 135 (this includes material flowing through the receptacle).

In certain particular aspects, there is only one vibratory apparatus 130*v*.

In one aspect, as shown in FIG. 18C, in a shaker 130*a* (like the shaker 130) a receptacle 135*a* (like the receptacle 135, FIG. 18A) is not in contact with the base 132 and is vibrated by apparatus 139*v*; or, if there is contact, it is via structure 139*s* made of material that does not conduct electricity. Optionally, as shown in FIG. 18C, a base or basket of a shaker may have a liner or container 132*b* therein that is made of material that does not conduct electricity and the liner or container 132*b* may have a piezoelectric system 138l or piezoelectric systems 138l which produce electric current when vibrated to kill living things in the liner or container 132*b*.

As shown in FIG. 18D, the introduction structure 134 may have an internal container 134*t*, liner or lining which contains material fed into the introduction structure. The container 134*t* is made of material that does not conduct electricity and it may have one or more piezoelectric systems therein like any disclosed herein.

It is within the scope of the present invention for the additional processing equipment APE and/or the further processing equipment FPE to include any structure or system herein for applying electric current to living things in such equipment. Optionally, it is within the scope of the present invention to provide a source of electric current ES, with appropriate connections, electrodes, wires, insulators, and/or insulating material to supply electric current to a shaker (or vibratory separator) and/or to screen(s) used therewith from a conventional current source ES (and this is true for any structure or system according to the present invention).

A control system CN (like any control system or apparatus disclosed or referred to herein; including control apparatuses and/or devices for controlling piezoelectric systems and/or for controlling a shale shaker and any motor, motors, or drive system used with shakers; which may be any suitable known control system for a shale shaker or vibratory separator), or multiple control systems, controls each item and piece of equipment and system in FIG. 19A.

FIG. 19A shows a system 140 according to the present invention for applying an electric current to material 146 within a vessel or container 142 that is vibrated by a vibratory apparatus 144. Within the vessel 142 are one or, as shown, a plurality of piezoelectric systems 148 which, when vibrated, produce electric current that flows to the material 146. As is true for any such system herein that is used to apply an electric current to material being processed, any suitable wires, electrodes, conductor arrangement, connections, and/or circuits are part of the piezoelectric systems 148 so that the current produced by the systems flows through the material 146. In one particular aspect, the material 146 is drilling fluid with living things therein and the applied electric current is sufficient to kill the living things. The systems 148 may be any suitable system herein according to the present invention.

A control system CO (like any control system of apparatus disclosed or referred to herein; including control apparatuses and/or devices for controlling piezoelectric systems and/or for controlling a shale shaker and any motor, motors, or drive system used with shakers; which may be any suitable known control system for a shale shaker or vibratory separator), or multiple control systems, controls each item and piece of equipment and system in FIG. 18A.

FIG. 19B shows a system 140*a* according to the present invention for applying an electric current to material 146*a* within a vessel or container 142*a* that is vibrated by a vibratory apparatus 144*a*. Within the vessel 142*a* are one or, as shown, a plurality of piezoelectric systems 148*a* which are floating in the material 146*a* and which, when vibrated, produce electric current that flows to the material 146*a*; and/or within the vessel 142*a* are one or, as shown, a plurality of piezoelectric systems 148*b* which are in the material 146*a* and sitting on, but not connected to, the bottom of the vessel 142*a* and which, when vibrated, produce electric current that flows to the material 146*a* As is true for any such system herein that is used to apply an electric current to material being processed, any suitable wires, electrodes, conductor arrangement, connections, and/or circuits are part of the piezoelectric systems 148*a* and/or 148*b* so that the current produced by the systems flows through the material 146*a*. In one particular aspect, the material 146*a* is drilling fluid with living things therein and the applied electric current is sufficient to kill the living things.

A control system CN (like any control system or apparatus disclosed or referred to herein; including control apparatuses and/or devices for controlling piezoelectric systems and/or for controlling a shale shaker and any motor, motors, or drive system used with shakers; which may be any suitable known control system for a shale shaker or vibratory separator), or multiple control systems, controls each item, system and piece of equipment and system in FIG. 19B.

The systems 148*a*, as shown in FIG. 19C have a body 148*m* within which is a piezoelectric system 148*s* which may be any suitable system herein according to the present invention. The body 148*m* is made of material of such a density that it floats in the material 146*a*. The systems 148*b*, as shown in FIG. 19D have a body 148*p* within which is a piezoelectric system 148*t* which may be any suitable system herein according to the present invention. The body 148*p* is made of material of such a density that it will not float in the material 146*a*.

In certain particular aspects, the body 142 is the material introduction structure and/or the basket of a vibratory separator or shale shaker. In certain particular aspects, the body 142 is made of material that does not conduct electricity. In certain particular aspects, the body 142*a* is the material introduction structure and/or the basket of a vibratory separator or shale shaker. In certain particular aspects, the body 142*a* is made of material that does not conduct electricity. In the aspects described in this paragraph, the tops of the containers 142 and 142*a* are optional and may be deleted if desired.

FIG. 20 illustrates a system 150 according to the present invention that applies a biocidal electric current to material 152 flowing over a conductive screening grid 154 of a screen 156 which has a frame 158 to which the screening material grid 154 is connected.

Electric current is applied to the grid 154 by an electric supply 151. Optionally, the frame 156 is made of material that does not conduct electricity. In certain aspects the material 152 itself conducts electricity between the connections of the supply 151.

In one particular aspect, the supply 151 applies a certain voltage across the connections to the screening material grid 154 and an optional voltage regulator system 153 operates in feed back with the circuit and the supply 151 so as to change the voltage as desired. The system 153 can include circuitry and a microprocessor 153*a* to measure data from the circuit and to determine the conductivity of the material 152 (and/or temperature) and these measurements can be used by the system 153, e.g., to effectively change the voltage applied to the circuit. Values of voltages can be stored in memory 153*b*.

In one particular aspect, the screen 156 is a screen for a shale shaker and the material 152 is drilling fluid. In one aspect, the drilling fluid has solids therein and the system 150 is used to heat the drilling fluid. In another aspect, the drilling fluid has living things in it and the system 150 is used to kill the living things. The supply 151 can be connected to or mounted on the shale shaker; or it can be separate therefrom, adjacent thereto or remote therefrom, with appropriate connections. The piezoelectric systems of FIG. 20 may be used with any control system or control apparatus referred to or described herein. In one aspect, the supply 151 is a piezoelectric system or systems.

FIG. 21 illustrates a system 160 according to the present invention that applies biocidal electric current to material 162 flowing over a conductive screening material grid 164 of a screen 166 which has a frame 168 to which the screening material grid 164 is connected. The screen 166 has a crossmember 167. Pairs of points on the screening material grid are connected to a piezoelectric system. Material between each pair of points completes an electrical circuit and then current from a piezoelectric system flows between the two points through the material being processed.

By way of illustration, pairs of points A-B, C-D, and E-F are each connected to a corresponding piezoelectric system 169*a* in or on the crossmember 167 which supplies electric current that flows between the points of the corresponding pair when the material 162 completes the circuit. By way of illustration, each pair of points G-H and I-J are connected to a corresponding piezoelectric system 169*b* which, when vibrated, produces electricity that flows between the points of the pair when the material 162 completes the circuit. Any desired number of pair points may be used and any desired number of systems 169*a*, 169*b* and/or 169*c* may be used. It is within the scope of the present invention to use a piezoelectric system or systems 169*c* in the frame 168.

Any piezoelectric system(s) in FIG. 16 may be used with the supply and/or controls of FIG. 15 and/or with any control system or apparatus disclosed or referred to herein. A control system CN (like any control system or apparatus disclosed or referred to herein; including control apparatuses and/or devices for controlling piezoelectric systems) controls the piezoelectric systems in FIG. 21.

FIG. 22 shows a shale shaker 190 (or vibratory separator) with electrical apparatus for applying an electric current to material being processed by the shaker to kill living things in the material, e.g., living things in drilling fluid. Any structure or member to which or in which electric current is applied in made of material that does not conduct electricity, including, but not limited to, nonconducting plastics; nonconducting fiberglass; and known composite materials used for shakers, components thereof, and shaker screens which materials do not conduct electricity. Any single point or area may be used for treating the material, e.g., but not limited to, in a supply tank 191; on a screen 192 (or screens if present); within a main basket 193; within an optional secondary basket 194 (e.g., a "scalping" basket); or in a receptacle 195 which receives material that passes through the screen(s) 192. Optionally the receptacle 195 is on a skid 197 and mounts 199 support the basket 193 above the skid 197.

Optionally a system as in FIG. 19 has all systems 198*a*-198*e* or only some of them. A drive system 190*s* vibrates the basket 193 (and the basket 194, if present). In one aspect, only a system 198*e* is used.

A system 198*a* provides electric current to the contents of the tank 191. A system 198*b* provides electric current to the material in the basket 194. A system 198*c* provides electric current to material on and/or flowing through the screen(s) 192. A system 198*d* provides electric current to material in the basket 193 hat has flowed through the screen(s) 192. The system 198*e* provides electric current to material in the receptacle 195. Each system 198*a*-198*e* has appropriate electrodes or wires or grids or conductors to apply the electric current produced by the systems; e.g., electrodes E (only two labeled). The systems 198*a*-198*e* may be outside of, adjacent, on or within the structures to which they correspond. Optionally, a single system is used to supply current to all the structures of the system 190.

A control system CL (like any control system or apparatus disclosed or referred to herein; including control apparatuses and/or devices for controlling piezoelectric systems and/or for controlling a shale shaker and any motor, motors, or drive system used with shakers; which may be any suitable known control system for a shale shaker or vibratory separator), or multiple control systems, controls each item, system, and piece of equipment and system in FIG. 22.

FIG. 23 shows a shale shaker (or vibratory separator) 200 according to the present invention which has the parts and structures that are labeled (similar to some of the parts and structures of the system 190, FIG. 21). Input stream 201 of material (e.g., drilling fluid with living things 202 therein), is introduced to the Tank and from there it is sent to and (partially) through the Screen(s), then the part of the material that passes through the screen(s) flows to the Receptacle. From the Receptacle output drilling fluid with living things 202 therein flows in a stream 207 to a vessel 204.

Optionally, an electric apparatus 205 is provided which applies an electric current to the stream 201, killing some or all of the living things 202 therein. The stream 201 can be fed into a vessel and the apparatus 205 can be on or in the vessel. Alternatively, as shown, the stream 201 flows between parts

205a and 205b (which are part of a circuit) of the apparatus 205 and current flows between these two parts through the stream 201, the completed circuit indicated by the dotted lines, and including as part of the circuit the material in the stream.

Optionally, an electric apparatus 206 is provided which applies an electric current to the stream 207, killing some or all of the living things 202 therein. The stream 207 flows between parts 206a and 265b of the apparatus 206 and current flows between these two parts and through the stream 201. Optionally or alternatively, the stream 207 can be fed into a vessel 209 in which with electric current some or all of the living things 202 are killed. This killing can be accomplished by one or more piezoelectric systems 208b and/or by a system 208a (like any system in FIG. 22 for applying a current to material).

A control system 204 (like any control system or apparatus disclosed or referred to herein) including control apparatuses and/or devices for controlling piezoelectric systems and/or for controlling a shale shaker and any motor, motors, or drive system used with shakers; which may be any suitable known control system for a shale shaker or vibratory separator, or multiple control systems, controls each item, system, and piece of equipment and system in FIG. 23.

It is within the scope of the present invention to use any known system for applying an electric current to the stream 201 and/or to the stream 207 and for applying a current to any stream of any embodiment herein; including, but not limited to, the systems disclosed in "High Speed Water Sterilization Using One-Dimensional Nanostructures" by Schoen et al, American Chemical Society, 2010, and any suitable system described or referred to in U.S. Patent Application Ser. No. 61/462,478 filed Feb. 3, 2011. It is also within the scope of the present invention to add any suitable known material to the stream 201 and/or to the stream 207 to increase or affect the conductivity of the stream(s) to enhance the conductivity thereof and/or to facilitate circuit completion by the material.

It is within the scope of the present invention for the features of any shale shaker or vibratory separator described above to be used with a shaker or separator that has a screen or screens at different levels or tiers, one above the other, or a part of one above all or above part of another. Any feature or aspect described above for heating material, heating a screen, heating a basket or any part of a shaker or separator, killing living things at any point or area of a shaker or separator, or killing living things in an initial feed stream or in an output stream can, according to the present invention, be used with a shaker or separator that has a screen or screens at different levels or tiers.

FIGS. 24A and 24B show a multi-level or multi-tier vibratory separator 210 according to the present invention which has four screening levels with screen supports 211, 212, 213, and 214 with a screen or screens 215 with screening material (shown schematically by lines labeled 215; any known shaker screen or screen and/or vibratory separator screen or screens may be used depending on the material to be processed). At any single level, any two levels, any three levels, or at all levels, the systems of the present invention described above may be used. In one aspect, the material processed by the separator 210 is drilling fluid with solids and/or living things therein.

Shown schematically, basket interior systems 218a (one or any desired number of them may be used) represent any apparatus, device or system disclosed herein for applying an electric current to material within a basket 210b (e.g., to kill living things in the material and/or to heat the material). Shown schematically, basket exterior systems 218b (of which at least part is outside the basket; one or any desired number of them may be used) represent any apparatus, device or system disclosed herein for applying an electric current to material within the basket 210b (e.g., to kill living things in the material and/or to heat the material).

Material which has flowed through or past all the screens flows into a receptacle 216. Shown schematically, receptacle interior systems 218d (one or any desired number of them may be used) represent any apparatus, device or system disclosed herein for applying an electric current to material within the receptacle 216 (e.g., to kill living things in the material and/or to heat the material).

Shown schematically, basket exterior systems 218c (of which at least part is outside the basket; one or any desired number of them may be used) represent any apparatus, device or system disclosed herein for applying an electric current to material within the receptacle 216 (e.g., to kill living things in the material and/or to heat the material).

Any screen or screen support of the separator 210 may have any or some of the systems described above for heating material on or adjacent the screen(s) and/or for killing living things in material (e.g., fluid) being processed with the screen(s). For example, shown schematically, screen systems 218e (one or any desired number of them may be used on one, some, or on all screens) represent any apparatus, device or system disclosed herein for applying an electric current to material being processed by the screen(s) (e.g., to kill living things in the material and/or to heat the material).

An input stream 217 of material to be treated flowing in a conduit 217a can be treated with an exterior system 218f, an exterior system 218g, and/or interior systems 218h (systems 218f and 218g have at least a portion thereof outside the conduit 217) (systems shown schematically) to heat and/or kill living things in the stream 217 and these systems can be any disclosed herein for these purposes.

An output stream 219 of material to be treated flowing in a conduit 219a can be treated with an exterior system 218k, an exterior system 218j, and/or interior system 218i (systems 218k and 218j have at least a portion thereof outside the conduit 219) (systems shown schematically) to heat and/or kill living things in the stream 219 and these systems can be any disclosed herein for these purposes.

Similarly, flow directors 211a, 212a, and/or 213a may have any system disclosed herein to heat material and/or to kill living things in material flowing on them.

The basket 215 of the separator 210 is on a skid 210s and has a control system 210c. In one particular aspect, the present invention provides improvements as described above to the subject matter of U.S. Pat. No. 7,703,612 which is incorporated fully herein for all purposes.

As can be easily understood from the foregoing, the basic concepts of the present invention may be embodied in a variety of ways. It involves both structures, method steps, and techniques as well as devices to accomplish the appropriate ends. In addition, while some devices and structures are disclosed, it should be understood that these not only accomplish certain methods but also can be varied in a number of ways.

The discussion herein is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure.

Where the invention is described in device-oriented or apparatus-oriented terminology, each element of the device or apparatus implicitly performs a function. Apparatus claims may not only be included for the device or apparatus described, but also method or process claims may be included to address the functions the invention and each element performs It should also be understood that a variety of changes may be made without departing from the essence of the invention. Such changes are also implicitly included in the description. They still fall within the scope of this invention.

It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners.

Each physical element disclosed should be understood to encompass a disclosure of the action which that physical element facilitates.

Thus, the applicants for this patent should be understood to have support to claim and make a statement of invention to at least: i) each of any described systems and new parts thereof as herein disclosed and described, ii) the related methods disclosed and described, iii) similar, equivalent, and even implicit variations of each of these systems, parts, and methods, iv) those alternative designs which accomplish each of the functions shown as are disclosed and described, v) those alternative designs and methods which accomplish each of the functions shown as are implicit to accomplish that which is disclosed and described, vi) each aspect, feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the inventors may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually waived or relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Any claims set forth at any time during the pendency of the application for this patent or offspring of it are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

In conclusion, therefore, it is seen that the present invention and the embodiments disclosed herein and those covered by the appended claims are well adapted to carry out the objectives and obtain the ends set forth.

Certain changes can be made in the subject matter without departing from the spirit and the scope of this invention. It is realized that changes are possible within the scope of this invention and it is further intended that each element or step recited herein is to be understood as referring to the step literally and/or to all equivalent elements or steps. It is intended to cover the invention as broadly as legally possible in whatever form it may be utilized.

The invention described herein is new and novel in accordance with 35 U.S.C. §102 and satisfies the conditions for patentability in §102. The invention described herein is not obvious in accordance with 35 U.S.C. §103 and satisfies the conditions for patentability in §103.

The inventor may rely on the Doctrine of Equivalents to determine and assess the scope of the invention. All patents and applications identified herein are incorporated fully herein for all purposes. The word "comprising" is used in its non-limiting sense.

What is claimed is:

1. A method for killing living things in a stream associated with a vibratory separator, the vibratory separator for treating a feed stream introduced to the vibratory separator, the method comprising
    with a killing apparatus, killing living things in a stream associated with the vibratory separator,
    wherein the killing apparatus applies electric current to the living things to kill the living things.

2. The method of claim 1 wherein the killing apparatus includes piezoelectric apparatus which produces the electric current in response to vibration of the vibratory separator.

3. A method for killing living things In a stream associated with a vibratory separator, the vibratory separator for treating a feed stream introduced to the vibratory separator, the method comprising
- with a killing apparatus, killing living things in a stream associated with the vibratory separator,
- wherein the vibratory separator is a shale shaker and the feed stream is drilling fluid with living things therein and with solids therein, the shale shaker being one of downfiow shaker and upfiow shaker, the method further comprising
- the shale shaker processing the drilling fluid producing a first output stream and a second output stream,
- the first output stream containing solids from the feed stream,
- the second output stream containing reusable drilling fluid,
- the stream associated with the vibratory separator being at least one of the first output stream, the second output stream, and the feed stream.

4. The method of claim 3 wherein the at least one of the first output stream, the second output stream, and the feed stream is the first stream.

5. The method of claim 3 wherein the at least one of the first output stream, the second output stream, and the feed stream Is the second stream.

6. The method of claim 3 wherein the killing apparatus provides killing material to the stream associated with the vibratory separator to kill living things, the method further comprising
- killing living things with the killing material.

7. The method of claim 3 wherein the killing apparatus applies electric current to the living things to kill the living things.

8. The method of claim 3 wherein the killing apparatus is a screen used in the shale shaker for treating the feed stream.

\* \* \* \* \*